United States Patent [19]

Lam et al.

[11] Patent Number: 5,424,185
[45] Date of Patent: * Jun. 13, 1995

[54] HUMAN HIGH-AFFINITY NEUROTRANSMITTER UPTAKE SYSTEM

[75] Inventors: Dominic M. Lam; Albert S. Chang, both of The Woodlands, Tex.

[73] Assignee: Baylor College of Medicine, Houston, Tex.

[*] Notice: The portion of the term of this patent subsequent to Jul. 6, 2010 has been disclaimed.

[21] Appl. No.: 586,443

[22] Filed: Sep. 21, 1990

Related U.S. Application Data

[63] Continuation-in-part of Ser. No. 342,238, Apr. 19, 1989, Pat. No. 5,225,323, and Ser. No. 274,328, Nov. 21, 1988, Pat. No. 5,188,954.

[51] Int. Cl.[6] .................... C12Q 1/68; C07H 21/04
[52] U.S. Cl. ............................ 435/6; 435/29; 435/172.3; 435/240.1; 435/240.2; 436/501; 436/92; 436/815; 436/816; 536/23.1; 530/350; 935/6; 935/9; 935/78
[58] Field of Search ............... 435/6, 29, 172.3, 69.1, 435/70.1, 70.3, 240.1, 240.2; 436/501, 92, 815, 816, 901; 530/350, 839; 536/27, 23.1; 935/6, 9, 70, 71, 77, 78

[56] References Cited

U.S. PATENT DOCUMENTS 4,675,285 1/1987 Clark et al. ........................ 435/6
4,985,352 1/1991 Julius et al. ....................... 435/6

OTHER PUBLICATIONS

*A Dictionary of Genetics* (Eds. King et al., Oxford University Press, New York, N.Y., 1968), p. 318.
Lowe et al. (1988) Journal of Cell Biology, vol. 106, pp. 51–59.
Yorek et al. (1987) Journal of Biological Chemistry, vol. 262, No. 23, pp. 10986–10993.
Lowe et al. (1988) J. of Cell Biol., vol. 106, pp. 51–59.
Old, R. W., "Principles of Gene Manipulation (1985) 2, p. 231 Blackwell Scientific Publications, London.
"Amino Acid and Putative Neurotransmitter Transport in Human Y79 Retinoblastoma Cells", *J. Biol. Chem.* (1987) 262(23), pp. 10986–10993 Yorek, et al.
Allen et al., "Isoproterenol response following transfection of the mouse $\beta_2$-adrenergic receptor gene into Y1 cells", *EMBO Journal* (1988) 7:133–138.
Asano et al., "Rabbit Brain Glucose Transporter Responds to Insulin When Expressed in Insulin–sensitive Chinese Hamster Ovary Cells", *The Journal of Biological Chemistry* (1989) 264:3416–3420.
Blakely, et al., "Expression of neurotransmitter transport from rat brain mRNA in *Xenopus laevis* oocytes", *Proc. Natl. Acad. Sci. USA* (1988) 85:9846–9850.
Burch and McBride, "Human Gene Expression in Rodent Cells after Uptake of Isolated Metaphase Chromosomes", *Proc. Natl.Acad. Sci. USA* (1975) 72:1797–1801.
Burk et al., "cDNA Cloning, Functional Expression, and mRNA Tissue Distribution of a Third Organellar $Ca^{2+}$ Pump", *The Journal of Biological Chemistry* (1989) 264:18561–18568.

(List continue on next page.)

Primary Examiner—Margaret Parr
Assistant Examiner—Ardin H. Marschel
Attorney, Agent, or Firm—Fulbright & Jaworski

[57] ABSTRACT

Non-primate or primate cells are provided comprising a functional human transporter for neurotransmitter uptake. The cells allow for dissection of the mechanism of neurotransmitter transport, as well as screening for agonists and antagonists of the neurotransmitter with respect to its uptake. Methods are provided for producing such cells. Specifically, the cells are transformed with human DNA comprising the gene encoding for the neurotransmitter transporter, whereby this protein(s) is expressed and incorporated into the plasma membrane and is capable of functioning to transfer the neurotransmitter from the extracellular space to intracellular domains. The physiological, kinetic and pharmacological characteristics of transport in these cells conform to known characteristics of high-affinity neurotransmitter transport in the CNS.

12 Claims, 2 Drawing Sheets

OTHER PUBLICATIONS

Chang et al., "Characterization of a genetically reconstituted high-affinity system for serotonin transport", *Proc. Natl. Acad. Sci. USA* (1989) 86:9611–9615.

Fraser et al, "Continuous High Density Expression of Human $\beta_2$-Adrenergic Receptors in a Mouse Cell Line Previously Lacking $\beta$-Receptors", *The Journal of Biological Chemistry* (1987) 262:14843–14846.

Hara et al, "Expression of sodium pump activities in BALB/c3T3 cells transfected with cDNA encoding $\alpha_3$-subunits of rat brain $Na^+$, $K^+$-ATPase", *FEBS* (1988) 238:27–30.

Jones et al., "Electrophysiological characterization of cloned m1 muscarinic receptors expressed in A9 L cells", *Proc. Natl. Acad. Sci. USA* (1988) 85:4056–4060.

Sardet et al., "Molecular Cloning, Primary Structure, and Expression of the Human Growth Factor-Activatable $Na^+/H^+$ Antiporter", *Cell* (1989) 56:271–280.

Sarthy, "$\gamma$-Aminobutyric acid (GABA) uptake by Xenopus oocytes injected with rat brain mRNA" Molecular Brain Research (1986) 1:97–100.

Takeyasu et al., "Ouabain-sensitive $Na^+ + K^+$-ATPase Activity Expressed in Mouse L Cells by Transfection with DNA Encoding the $\alpha$-Subunit of an Avian Sodium Pump", The Journal of Biological Chemistry (1988) 263:4347–4354.

Underhill and Flintoff, "Complementation of a Methotrexate Uptake Defect in Chinese Hamster Ovary Cells by DNA-Mediated Gene Transfer", *Molecular and Cellular Biology* (1989) 9:1754–1758.

Dingledine et al., "Amino Acid Receptors and Uptake in the Mammalian Central Nervous System", *CRC Critical Reviews of Neurology* (1988) 4, (1) pp. 1–96.

Albert et al., "Cloning, Functional Expression, and mRNA Tissue Distribution of the Rat 5-Hydroxytryptamine$_{1A}$ Receptor Gene" by The *Journal of Biological Chemistry* (1990) 265:5825–5832.

Allen et al., "$\beta_2$-Adrenergic Receptor Regulation after Transfection into a Cell Line Deficient in the cAMP-Dependent Protein Kinase", *Molecular Pharmacolo* (1989) 36:248–255.

Bannon, et al., "Expression of a Human Cocaine-Sensitive Dopamine Transporter in *Xenopus laevis* Oocytes", *Journal of Neurochemistry* (1990) 54:706–708.

Birnir et al., "Expression and characterization of the intestinal $Na^+$/glucose cotransporter in COS-7 cells", *Biochimica et Biophysica Acta* (1990) 1048:100–104.

Buc-Caron et al., "Serotonin uptake, storage, and synthesis in an immortalized committed cell line derived from mouse teratocarcinoma", *Proc. Natl. Acad. Sci. USA* (1990) 87:1922–1926.

Byers et al., "Expression of a human gene for polyamine transport in Chinesehamster ovary cells" *Biochem. J.*, (1989) 263:745–752.

Claudio, et al., "Fibroblasts Transfected with *Torpedo* Acetylcholine Receptor $\beta$-, $\gamma$-, and $\delta$-Subunit cDNAs Express Functional Receptors When Infected with a Retroviral $\alpha$ Recombinant", The Journal of Cell Biology, (1989) 108:2277–2290.

Graeve et al., "Polarized Endocytosis by madin-Darby Canine Kidney Cells Transfected with functional Chicken Liver Glycoprotein Receptor", The Journal of Cell Biology (1989) 109:2809–2810.

Hofmann et al., "Overexpression of Human Low Density Lipoprotein Receptors Leads to Accelerated Catabolism of Lp(a)Lipoprotein in Transgenic Mice", J. Clin. Invest. (1990) 85:1542–1547.

Shapiro, et al., "Characterization and functional expression in mammalian cells of genomic and cDNA clones encoding a *Drosophila* muscarinic acetylcholine receptor", Proc. Natl. Acad. Sci. USA (1989) 86:9039–9043.

Sontheimer et al., "Functional Chloride Channels by Mammalian Cell Expression of Ray Glycine Receptor Subunit", *Neuron* (1989) 2:1491–1497.

White & Weber, "The *src* Oncogene Can Regulate a Human Glucose Transporter Expressed in Chicken Embryo fibroblasts" *molecular and Cellular Biology* (1990) 10:1301–1306.

Dearry et al., "Molecular Cloning and Expressin of the Gene for a Human $D_1$ Dopamine Receptor", *Nature*, Sep. 6, 1990 347, pp. 72–75.

Zhou et al., "Cloning and Expression of Human and Rat $D_1$ Dopamine Receptors", *Nature*, Sep. 6, 1990 347, pp. 76–79.

Sunahara et al., "Human Dopamine $D_1$ Receptor Encoded By An Intronless Gene On Chromosome 5", *Nature*, Sep. 6, 1990 347, pp. 80–83.

Sokoloff et al., "Molecular Cloning and Characterization of a Novel Dopamine Receptor ($D_3$) as a Target for Neuroleptics", *Nature*, Sep. 13, 1990 347, pp. 146–150.

Harrison et al., "Insulin Action on Activity and Cell Surface Disposition of Human HepG2 Transporters expressed in Chinese Hamster Ovary Cells", J. Biol. Chem. Apr. 5, 1990 265, pp. 5793–5081.

HUMAN HIGH-AFFINITY NEUROTRANSMITTER UPTAKE SYSTEM

CROSS-REFERENCE TO RELATED APPLICATIONS

This application is a continuation-in-part of U.S. Ser. No. 342,238, filed Apr. 19, 1989, now issued as U.S. Pat. No. 5,225,323, and U.S. Ser. No. 274,328, filed Nov. 21, 1988 now issued as U.S. Pat. No. 5,188,954, which disclosures are hereby incorporated herein by reference. This invention was made with Government support under Grant No. EY02423 awarded by the National Institutes of Health/National Eye Institute. The Government may have certain rights in this invention.

INTRODUCTION

Technical Field

This invention relates to high-affinity human neurotransmitter transporters introduced into cultured cells and methods of use of these cells, in particular for identifying agonists and antagonists of the neurotransmitter transporters.

Background

An essential regulatory step in neurotransmission in both the central and peripheral nervous systems is the inactivation of the neurotransmitter following its release into the synaptic cleft. For biogenic amine and amino acid neurotransmitters, uptake of the released neurotransmitter is the most common mechanism for inactivation. In the central nervous system, the uptake is accomplished by glial cells and/or by the reuptake system (transporters) of the presynaptic neuron. These transporters, which reduce intersynaptic concentration of neurotransmitters, are characteristically ion dependent, of high-affinity, and are temperature sensitive.

High-affinity neurotransmitter transport systems are currently believed to be intimately involved in both the neuropathology and therapeutic treatment of certain neurological disorders, including depression, epilepsy, schizophrenia, Parkinsonism, and eating and sleeping disorders. Amelioration of these and other nervous disorder symptoms frequently involves manipulation of transmitter levels in the affected tissues. In some instances alleviation of these disorders is mediated by the use of pharmaceutical agents specific for neurotransmitter transport systems which may be the same as or different from agents specific for neurotransmitter receptor systems. Application of an appropriate antagonist to block uptake prolongs and enhances the action of the neurotransmitter. For example, serotonin and norepinephrine uptake blockers (e.g. imipramine) are used as antidepressants, and benztropine, an antagonist of dopamine uptake, temporarily alleviates the symptoms of Parkinson's disease. Epilepsy can be treated with blockers of γ-amino butyric acid (GABA) uptake.

Methods for evaluating other potential therapeutic agents are hampered by the lack of an adequate system for studying these agents. Intact neural tissue, primary neuronal/glial cultures, brain-derived tumor cell lines such as neuroblastoma/glioma cell lines, synaptosomal and membrane vesicle preparations, brain slices and animal brain homogenates have been used to investigate in vitro the processes involved with neuronal uptake. However, these systems suffer from substantial limitations, including the difficulty of establishing systems which are homogenous in both neurochemical and neurophysiological composition, well defined in terms of growth and maintenance requirements, and neurophysiologically and neurochemically stable over time. These systems also do not lend themselves readily to use on a large scale.

Other methods used for screening of potential therapeutic agents include the use of membrane receptor assays. However, it has recently become clear that there may be distinct differences between neurotransmitter receptors and neurotransmitter transporter systems and the relationship of each system to a particular nervous disorder. At least in some instances, only the transporter system may be involved. Therefore, it is of interest to develop an in vitro system which can be used to investigate the mechanisms of transmitter-specific transport (uptake) systems in depth, as well as to evaluate potential agonists and antagonists of the uptake system, particularly where the system is relatively insulated from other cellular components which may affect the specific neurotransmitter transport system under investigation.

Relevant Literature

Expression of a human serotonin transport system in mouse fibroblast L-M cells is described by Chang, et al., *Proc. Natl. Acad. Sci.* (USA), (1989) 86:9611–9615. The principal coauthors of this publication are the inventors of the subject application. Expression of a mouse serotonin uptake system in an immortalized mouse teratocarcinoma is described by Buc-Carron et al., *Proc. Natl. Acad. Sci.* (USA), (1990) 87:1922–1926. Expression of a dopamine transporter following injection of mRNA isolated from human brain substantia nigra into Xenopus oocytes has been described by Bannon et al., *J. Neurochemistry* (1990) 54:706–708. Poly(A)+ RNA isolated from rat nervous systems and injected into Xenopus oocytes induces the expression of uptake systems for L-glutamate, γ-aminobutyric acid, glycine, dopamine, serotonin and choline was described by Blakely et al., *Proc. Natl. Acad. Sci.* (USA) (1988) 85:9846–9850. γ-Aminobutyric acid (GABA) uptake by *Xenopus oocytes* injected with rat brain mRNA has been reported by Sarthy, *Molecular Brain Research* (1986) 1:97–100.

The expression of exogenously introduced DNA has been described for established cell lines by Wigler et al, *Cell* (1979) 16:777–785; Kuhn, et al., *Mol. Biol. Med.* (1983) 1:335–352; Chao, et al., *Science* (1986) 232:418–421; and Greco, et al., *Proc. Natl. Acad. Sci. USA* (1987) 84:1565–1569. Transformation of mouse cells with plasmids comprising a viral transfection system is described by Southern and Berg, *J. Mol. Appl. Genet.* (1982) 1:327–341.

SUMMARY OF THE INVENTION

Novel transgenic cell lines expressing neurotransmitter transporters and methods for their preparation are provided. Host cells capable of stable maintenance in culture are transformed with a DNA sequence encoding a neurotransmitter transporter. The resulting transgenic cells are characterized as being capable of at least substantially specifically transporting a neurotransmitter of interest, with uptake of the neurotransmitter being ion dependent, saturable and temperature sensitive. The transgenic cells find use for screening potential agonists or antagonists of neurotransmitter transporters.

DESCRIPTION OF THE SPECIFIC EMBODIMENTS

Transgenic cells, particularly mammalian cells, more particularly non-primate vertebrate cells, capable of stable growth in culture are provided which comprise a functional primate, particularly human, neurotransmitter uptake system (transporter). Methods are provided for preparing these cells, as well as for using the cells for investigation of neurotransmitter transport mechanisms and screening for potential agonists and antagonists of a neurotransmitter transport system of interest. Cell lines established from these transgenic cells can stably manifest high-affinity neurotransmitter transport systems over an extended period of time.

The cell lines offer several advantages over other models used for identification and development of transport specific drugs. Clonal cell lines can be identified that each manifest a single high-affinity neurotransmitter transport system devoid of any other neurotransmitter membrane phenotype, including transport systems, receptors, degrading enzymes, and the like due to the fibroblastic nature of the transfection host cell. Thus each high-affinity neurotransmitter transport system can be analyzed in isolation in terms of its transport mechanisms and pharmacological profiles without interference or distortion by other neurotransmitter-related systems.

Other advantages include that the clonal cell lines can be maintained in culture for extended periods of time, for example several months to years, thereby providing a continuous supply of assay substrate with relatively homogeneous and consistent levels of transport capability. The high-affinity neurotransmitter transport systems in these clonal cell lines possess all of the kinetic, physiological and pharmacological properties of the transport systems as measured in animal-derived tissues. The use of transfectant cell lines in the studies of transport systems thus has the additional advantage that it obviates the need for use of large numbers of animals for uptake system studies.

The host cells of this invention will, for the most part, be non-primate vertebrate cells derived from rodentia, lagomorpha, equine, bovine, porcine and the like, more particularly murine tissues and organs. Cells of primate origin may also be used as host cells when appropriate. The host cells will generally be other than those associated with the brain (neurons, glial cells, and the like) or other tissues or organs having neurotransmitter related structures such as receptors and uptake systems. Thus the cells may be derived from skin, for example fibroblasts; and may be epithelial cells derived from a variety of tissues and organs including muscle, bone, and the like. Cells of particular interest are those which under in vitro or culture conditions do not manifest high rates of genetic recombination, and which may be easily grown under culture conditions such that they stably retain the exogenous DNA and continuously undergo mitotic divisions at definable rates. Cell lines which may find particular use as host cells include mouse L-M fibroblasts, L-TK$^-$ fibroblasts, L-929 fibroblasts and 3T3 fibroblasts.

The neurotransmitter uptake systems or transporters which may be introduced into a host cell include the transporters for biogenic amines such as serotonin, dopamine, epinephrine, norepinephrine, and amino acids such as L-glycine and L-glutamate, L-aspartate, and γ-aminobutyric acid (GABA). By "transporter" is meant a cellular uptake system which, under physiologic conditions of pH, temperature and the like, is at least substantially specific for at least one neurotransmitter. Further, uptake and accumulation of the neurotransmitter may be characterized as (a) inhibited by known agonists and antagonists of the neurotransmitter uptake system in vivo; (b) ion or temperature dependent or both; (c) kinetically saturable; and (d) characterized as possessing high-affinity for the given neurotransmitter. By "high-affinity" is intended a K$_m$ of at most about $10^{-5}$M, preferably $10^{-6}$M to $10^{-7}$M, more preferably about $10^{-8}$M, for the endogenous neurotransmitter associated with the transporter.

The exogenous DNA encoding the transporter may be introduced into the host cell in a variety of ways. Conveniently, the host cell may be transformed with human genomic DNA encoding the transporter in the presence of a DNA sequence which provides for a selection marker. Thus, human genomic DNA may be prepared, as intact chromosomes or as degraded DNA fragments, being from about 5 to 100 kbp in size, and mixed with a plasmid or linear DNA capable of stable maintenance or integration into the genome of the host cell and encoding a selection marker. Conveniently, calcium phosphate precipitation may be employed as described in the literature. For example, the DNA may be dissolved in an appropriate phosphate buffered saline solution, about pH 7, and an equal volume of about 0.1–0.5M calcium chloride added drop-wise. The resulting precipitate is incubated, followed by adding to the cells and incubating for an extended period of time, usually for at least about 8 hours and for not more than about 24 hours. The cells then are separated from the precipitate and cultured in the presence of a selection agent to select for transgenic cells.

The particular manner of selection is not critical to this invention. For the most part resistance to cytotoxic agents is convenient. Various antibiotics may be employed, but particularly convenient combinations are a neomycin resistance gene APH(3')II with G418, or the DHFR gene in combination with methotrexate. Resistant cells containing a specific transporter may be identified by, for example, exposure to radiolabelled neurotransmitter following treatment with the cytotoxic agent. The selectable marker gene may be associated with a replication system, since the combination of the gene with a replication system generally provides for a larger number of transformed cells which may be selected. Various replication systems are available as derivatives of SV40, bovine papilloma virus, adenovirus, etc. These vectors find ample description in the literature.

Transformation with genomic DNA avoids the difficulties of identifying mRNA or the genomic sequence encoding the transporter. However, rather than transform the host cells with genomic DNA, one may transform with the appropriate transporter gene, where such gene is available. If such DNA sequence is available, this sequence may then be used for transformation in accordance with known techniques. It may be desirable to replace the transcriptional initiation region of the transporter gene with a host cell transcriptional initiation region. In some cases this would not be desirable, for example, where the transporter transcriptional region is subject to different conditions for induction from those of the host cell transcriptional initiation region and it is of interest to determine the induction mechanism and/or the effect of compounds on such induction of expression of the transporter in its cell of origin.

The joining of the transporter gene to a replication system and transformation of the host cells with the resulting plasmids is well known in the literature and the transporter gene could be introduced into a plasmid comprising a marker plasmid, so that the host cell would be simultaneously transformed with the marker and the transporter gene. Selection would follow in the same way as selection occurred for cotransfection of a marker plasmid and genomic DNA.

Transgenic cells can be selected based on resistance to the cytotoxic agent. Transformed colonies are exposed to the cytotoxic agent, followed by uptake of labelled, generally a radioactively-labelled, neurotransmitter of interest. After contacting the transformed cell colonies with the labelled neurotransmitter, and incubating for sufficient time, usually from about 0.5 to about 2 hours at physiological temperature and pH, the cells are thoroughly washed to remove any extracellular neurotransmitter. The presence of the neurotransmitter intracellularly may then be determined by means of the label. Conveniently, a radiolabel is employed. Desirably, the results from different colonies are normalized to correct for differences in the number of cells or levels of expression in individual cells, for example, by assaying for alkaline phosphatase activity or by protein quantitation.

In order to ensure that the neurotransmitter uptake is related to expression of the human transporter gene, the cell colonies may be further screened to demonstrate that the neurotransmitter uptake is dependent upon conditions and ancillary compounds associated with in vivo neurotransmitter uptake. For example, where the neurotransmitter is serotonin, which is both sodium ion dependent and temperature dependent, a showing of temperature and sodium dependence of serotonin uptake would be indicative of serotonin uptake via a serotonin transporter. In addition, agonists and antagonists of the transmitter transport system may be employed, for example, by use of imipramine which inhibits neuronal uptake of serotonin and demonstrate that the uptake is appropriately sensitive to the presence of known agonists and antagonists. Furthermore, rigorous kinetic measurements can be employed to establish the affinity and capacity of the neurotransmitter uptake system as being in agreement with high-affinity uptake systems detected in vivo. In order to obtain a clonal cell line, comprising transgenic cells having transporter capacity, the cells may be cloned so as to provide a monoclonal cell line. The cells may be cloned using techniques known to those skilled in the art, for example by limiting dilution, and the like.

Once the cells have been established as cell lines and have been identified as specifically transporting a particular neurotransmitter and that the transport of the neurotransmitter is sensitive to the same agents and conditions associated with the neurotransmitter transporter present in vivo, the cells may then be used in a variety of ways. The cells may be used in research for investigating the mechanism of the neurotransmitter interacting with its receptor. The host cell may additionally be transformed with other human genes(s) to determine what effect the expression of the additional human gene(s) has on the functioning of the neurotransmitter transporter. In this way, the presence of associations which may have specific effects on the functioning of the neurotransmitter transporter may be determined. One may relate changes in plasma membrane potential of the cell, by identifying certain channels associated with the functioning of the transport systems. In addition, one may change the ionic strength in the medium in which the cell is grown or the concentration of a specific ion to investigate its effects on transport mechanisms.

Of particular interest is the use of the transformed host cells for screening compounds for agonist or antagonist activity on transport systems. The availability of invariant cell lines, which retain fibroblast characteristics and can be maintained in continuous culture, facilitates rapid assays of novel drugs potentially useful for the treatment of disorders believed to be associated with neurotransmitter uptake. For example, serotonin uptake is associated with depression and anxiety (Soubrie, P., *Neuronal Serotonin* (Eds. Osborne, N. N. and Hamon, M.) (1988) pp. 255–270 and Barnes, D. M., *Science* (1988) 241:1029–1030); obesity (Blundell, J. E. *Appetite* 7 *Suppl.* (1986) pp. 39–56 and Silverstone, T. et al., *Appetite* 7 *Supple.* (1986) pp. 85–97); alcoholism (Gill, K. et al., Alcoholism II, (1987), pp. 444–449 and Naranjo et al., *Clin. Pharmacol. Ther.*, 41:266–274 (1987); postanoxic intention myoclonus (Van Woert, M. H. et al., *Monogr. Neural. Sci.* (1976) 3:71–80); acute and chronic pain (Le Bars, D. *Neuronal Serotonin* (Eds. Osborne M. N. and Hamin, M.) (1988) pp. 171–229); as well as sleep disorders (Koella, W. P. *Neuronal Serotonin* (Eds. Osborne, M. M. and Hamon, M.) (1988) pp. 153–170).

By measuring the amount of neurotransmitter which is transported into the transformed host cells in the presence or absence of the investigatory or candidate compound, one can evaluate the role of the compound. Agonists will be distinguished from antagonists, where transport of the neurotransmitter is associated with a specific function which is observable with the cell such as an increase or decrease in the intracellular concentration of radiolabelled neurotransmitter. Where such specific function occurs, the compounds may be further screened using the transformed host cells to determine the specific extent to which the compound acts as either an agonist or antagonist. Thus, the subject transformed host cells provide for an efficient and precise means for screening compounds which can competitively bind to the neurotransmitter transporter, so as to compete for, and either prevent or enhance the binding or transport (uptake) of the natural neurotransmitter.

From an immunological standpoint, these cells can also be used to produce polyclonal and monoclonal antibodies specifically reactive with the transporter of interest. A transgenic cell line containing a neurotransmitter transporter of interest is used as the immunogen. Blood from the immunized animal can be screened using transgenic cells (and untransfected cells as controls) via enzyme-linked immunosorbent assay (ELISA). The existence of such antibody would facilitate the purification of the transporter from which structure function relationships could be elucidated. Such antibodies can also be used in diagnostics, for example in determining changes in expressed levels of a given transporter in a patient specimen as a means of diagnosing a particular nervous disorder, for example, where a decrease in the number of transporter molecules is indicative of a particular disease state.

Since the presence of human DNA in the transgenic cells is coincidental with the expression of uptake systems, it may be surmised that these systems are encoded by human gene(s) having been integrated into the genome of transfected cells. Hence the transgenic cells are potential substrates from which to clone and identify transporter genes. One such cloning strategy would necessarily rely on human Alu repetitive sequences as a discriminating hybridization probe to distinguish human from mouse DNA (Hwu, H. R. et al., PNAS (1986) 83:3875-3879) and for isolating and identifying specific human DNA fragments having integrated in transgenic cells expressing the transport system of interest. These fragments can be used systematically to delineate the actual genomic structure of the transporter genes.

Depending upon the number of Alu hybridizing fragments, the identification of the genes encoding the transporters could be facilitated by construction of a genomic library from which to identify DNA clones that contain Alu sequences. Analysis of the DNA clones by transfection and subsequent expression and RNA blotting should then lead to identification of the clones which contain the transporter gene/locus. Alternatively, it is logical to assume that these transfectant cells contain mRNAs which are expressed as membrane proteins not present in the untransfected host cells. RNA subtraction should yield a number of mRNA species present in the transfectant cells but not in non-transfectant cells. The resulting mRNAS could be transcribed into cDNAs and be analyzed individually in an attempt to identify and characterize the transporter gene. Either by genomic or mRNA approaches, the chimeric nature of the transgenic cell lines can be used to design cloning strategies to obtain primary structure of the transporters and for determining the biophysical and biochemical parameters of the uptake systems.

The invention now being generally described, the same will be better understood by reference to the following examples which are provided for purposes of illustration only and are not to be considered limiting of the invention unless so specified.

| EXPERIMENTAL Table of Contents | |
|---|---|
| Example I | Preparation of Transgenic Cells Comprising Transporters |
| Example II | Transgenic Cells Containing a Serotonin Transporter |
| Example III | Transgenic Cells Containing Glycine a Transporter |
| Example IV | Transgenic Cells Containing a Dopamine Transporter |
| Example V | Transgenic Cells Containing High-Affinity L-glutamate Transporter |
| Example VI | Transgenic Cells Containing a High-Affinity γ-aminobutyric Acid (GABA) Transporter |
| Example VII | Transgenic Cells Containing a High-Affinity D- and L-aspartate (Asp) Transporter |

Materials

[$^3$H]-5-hydroxytryptamine binoxalate (28.8 Ci/mmole) was purchased from New England Nuclear. Dulbecco's Modified Eagle Medium (DMEM) and penicillin/streptomycin were obtained from GIBCO. Defined Fetal Bovine Serum (dFBS) was a product of Hyclone. Fluoxetine was graciously donated by Eli Lilly, Indianapolis, Ind., and mianserin was purchased from Research Biochemicals, Natick, Mass. Pargyline, amino acids, neurotransmitters, and other 5-HT uptake inhibitors were purchased from Sigma Chemical Co., St. Louis, Mo. All other materials and supplies were obtained from commercial sources.

Maintenance and Preparation of Cell Lines

All cell lines were grown in continuous culture in DMEM supplemented with 10% dFBS and 1% penicillin/streptomycin. Cells were trypsinized and plated into 96 well plates such that each well became confluent after 2–3 days in culture.

Abbreviations Used

5-HT (serotonin), GABA (γ-aminobutyric acid), DA (dopamine), DOPA (L-dopa), EP (epinephrine), NE (norepinephrine), TRP (tryptophan), TYR (tyrosine), PHE (phenylalanine).

EXAMPLE I

Preparation Of Transgenic Cells Comprising Transporters

Calcium phosphate precipitation (Graham & Van der Eb (1973) Virology 52:456-467) is an efficient means of introducing exogenous DNA into mouse fibroblast L cells. This method was used to cotransfect into L-M cells human genomic DNA and pSV2neo, a neomycin resistance-bearing plasmid capable of rendering eukaryotic cells resistant to G418 (Southern & Berg J. Mol. Appl. Genet. (1982) 1:327-341). Our studies indicated that L-M cells were sensitive to the presence of 400 μg/ml G418 in the culture medium. This was the antibiotic concentration used to select for cell-transfectants, and gave rise to over 10,000 G418-resistant clones following one transfection experiment.

Mouse L-M fibroblast cells (ATCC CCL 1.2) were cultured in Dulbecco's modified Eagles Medium (GIBCO) supplemented with 10% defined Bovine Serum (Hyclone, Inc.) and 1% penicillin/streptomycin (GIBCO). Cells were preplated in 100mm culture dishes such that by the time of transfection the cell number would be about $10^6$ cells per dish. Human genomic DNA 30 μg) and pSV2neo (Southern and Berg, supra) (0.1 μg) were combined in 280 mMNaCl, 10 mM KCl, 1.5 mM Na$_2$HPO$_4$, 10 mM glucose, 50 mM HEPES, p 7.05, and an equal volume of 0.25M CaCl$_2$ was added dropwise. The precipitate was kept at room temperature for approximately 30 min before being mixed with culture medium and added to L-M cells for 16 hrs. The precipitate mixture was then removed and the cells replated onto 96-well plates and grown in the presence of G418 (GIBCO; 400 µg/ml) until transfectant colonies were well-established.

Typically, each well contained 3-5 colonies following G418-selection. Each well containing transfectant colonies was then trypsinized and replated into separate sets for both assays and cell-stocks.

EXAMPLE II

Transgenic Cells Containing a Serotonin Transporter a. Screening for Serotonin Uptake

During the initial screening, the entire bank of transfectants were assayed for [$^3$H]-serotonin uptake. To perform the uptake assay on 96-well plates, the culture medium from each well was first removed, the cells rinsed twice with oxygenated Ringer's solution (128 mM NaCl, 5.2 mMKCl, 2.1 mM $CaCl_2$, 2.9 mM $MgSO_4$, 5 mM glucose, 10 mMHEPES, pH 7.4, supplemented with 0.5 mM ascorbate, 0.5 mM pargyline) and then incubated with 50 µl of Ringer's solution plus 0.1 µM [$^3$H]-serotonin for 40 min at 37° C. The incubation mixture was then removed and each well washed three times before adding 50 µl of alkaline phosphatase buffer: 100 mMTris, pH 9.5, 100 mM NaCl, 10 mM/$MgCl_2$, 20 µg/ml saponin, 3.2 mg/ml p-nitrophenyl phosphate.

The phosphatase assay was employed as a rapid and convenient measure of relative cell number for each well and served as a normalizing measure to expedite data analyses. The reaction was conducted for 1-2 hrs. at 37° C., and terminated with addition of 100 µl 1% SDS to each well. The extent of the phosphatase reaction for each well was measured at $A_{405}$ nm with an automated ELISA reader. The [$^3$H]-content of each well was then determined by scintillation counting. The data for all the assayed wells were then plotted as the cpm of tritium associated with each well versus its corresponding phosphatase reading.

The majority of the data points clustered together in a "main cluster" represented by a linear positive slope. In contrast, the rare high respondents in the assay can be identified as relatively high points above the cluster. The wells containing the high respondents were then expanded from stock plates and rescreened to ensure consistency of high responses.

b. Specificity of Serotonin Transporter

Those wells containing high respondent transgenic cells were also tested with imipramine, a known antagonist of serotonin uptake. For such inhibition assays, the cells in each well were preincubated with Ringer's solution plus 10 µM imipramine at 37° C. for 10 min. [$^3$H]-serotonin was then added to each well to provide a final concentration of 0.1 µM. The cells were incubated at 37° C. for an additional 40 min. Cells demonstrating both high levels of [$^3$H]-serotonin uptake and imipramine antagonism during the second screening were then cloned as single-cell cultures.

Cells derived from the single-cell clones were again tested for both the extent of [$^3$H]-serotonin uptake, as compared with untransformed L-M cells, and imipramine antagonism. In this manner, transformed strains L-S1 and L-S2 were identified as monoclones possessing the desired characteristics.

To further demonstrate that the radioactivity measured in L-S1 represented transport of [$^3$H]-serotonin into these cells, autoradiography was carried out on these cells following incubation with [$^3$H]-serotonin. Most of the radioactivity was located inside the cells, rather than binding to the cell surface. When analyzed by reverse-phase HPLC, over 90% of the radioactivity inside the L-S1 cells comigrated with [$^3$H]-serotonin.

c. Ion Dependence

Uptake assays of [$^3$H]-serotonin by L-S1 and L-M were performed with Ringer's solution of varying ionic compositions or different assay temperatures. All assays were performed by incubating the cells with 0.1 µM [$^3$H]-serotonin for 40 min. For $Na^+$-dependence, the uptake level of L-S1 with normal Ringer's solution ("+Na" in Table I) was set at 100% and used to normalize the uptake levels of L-S1 and L-M assayed in the absence of $Na^+$. Sucrose supplementation was used to obtain $Na^+$-deficient Ringers ("−Na" in Table I) by using 256 mM of sucrose to iso-osmotically replace 128 mM of NaCl in making the Ringer's solution while all other components remained invariant. Similarly, $Ca^{2+}$-dependence was tested by setting L-S1 uptake levels in normal Ringer's solution ("Na+Ca") at 100% and then comparing to uptake levels in Ringer's solution wherein $Ca^{2+}$ was replaced by $Co^{2+}$ ("Na+Co") or $Mg^{2+}$ ("Na+Mg"). Uptake into untransformed L-M cells was used as a control. The results for L-S1 cells are shown in Table 1 below. Both L-S1 and L-S2 cells exhibit dependences on $Na^+$ for their 5HT transport activities, but not $Ca^{2+}$ dependency.

d. Temperature Dependence

Temperature-dependence was tested by performing the uptake assay at both 37° C. and 0° C. (on ice). Prior to each assay, the cells were first allowed to equilibrate to the desired temperature for 10 min. L-S1 assayed at 37° C. was set as 100% level, against which data obtained for 0° C. were normalized. All data were first converted to cpm/mg protein prior to normalization against L-S1 uptake levels. The results are shown in Table I, below, only for L-S1 cells. Both L-S1 and L-S2 cells exhibit strong temperature dependency on 5HT uptake.

TABLE I

ION AND TEMPERATURE DEPENDENCIES OF [$^3$H]-SEROTONIN UPTAKE BY L-S1

|  |  | L-S1 (%) | L-M (%) |
|---|---|---|---|
| Sodium: | +Na | 100.0 | 18.90 ± 2.07 |
|  | −Na | 12.37 ± 1.66 | 11.46 ± 1.28 |
| Calcium: | Na + Ca | 100.0 | 17.30 ± 1.70 |
|  | Na + Co | 97.64 ± 10.62 | 16.12 ± 1.44 |
|  | Na + Mg | 98.56 ± 10.09 | 18.48 ± 1.57 |
| Temp.: | 37° C. | 100.00 | 11.70 ± 1.04 |
|  | 0° C. | 2.77 ± 0.29 | 1.36 ± 0.07 | e. Specificity of Serotonin Transporters

The specificity of [$^3$H]-serotonin uptake by L-S1 and L-M cells was determined as follows. L-S1 and L-M cells were preplated into 96-well culture plates. For uptake assays, the growth medium was removed from each well and the cells rinsed several times with oxygenated Ringer's buffer supplemented with 0.5 mM pargyline and 0.5 mM ascorbate. Cells were preincubated with competing neurotransmitters or amino acids (each at 10 µM) at 37° C. for 10 minutes prior to the addition of [$^3$H]-5HT. The radioligand was added to a final concentration of 0.1 μM and incubated with the cells at 37° C. for 40 minutes. The incubation mixture was then removed and each well was washed three times at room temperature with Ringer's buffer. The cells remaining in the wells were lysed with 1% sodium dodecyl sulphate (SDS) and transferred to counting vials containing 5 ml of ACS scintillant (Amersham), for liquid scintillation spectrometry. For each assay, 6–8 parallel sets of wells were assayed simultaneously. Additional sets were processed in the same manner for protein determination by the BCA assay (Smith et al., *Analytical Biochemistry* (1985) 150:76–85). The extent of [$^3$H]-serotonin accumulation in each well was then normalized by its protein content and expressed as "cpm/mg protein" for comparison purposes.

Figure 1:
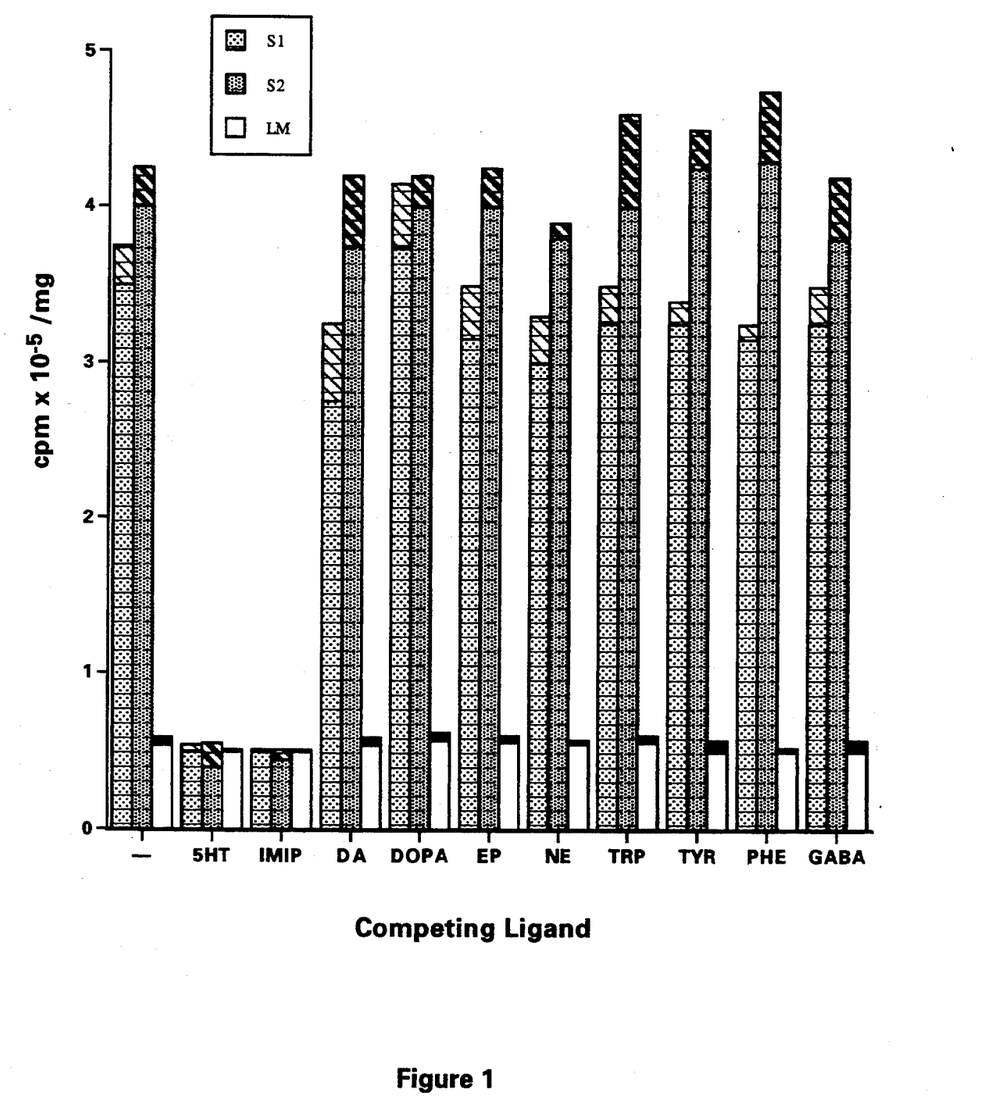
FIG. 1 shows neurotransmitter specificity of [$^3$H]-5HT uptake. L-S1, L-S2, and LM cells were assayed in the absence or presence of competing ligands: 5HT (serotonin), IMIP (imipramine), DA (dopamine), DOPA (L-dopa), EP (epinephrine), NE (norepinephrine), TRP (tryptophan), TYR (tyrosine), PHE (phenylalanine), GABA (γ-aminobutyric acid). Each competing ligand, at a concentration of 10 μM, was preincubated with cells for 10 minutes prior to the uptake assay with 0.1 μM [$^3$H]-5HT at 37° C. for 40 minutes. Each bar represents the mean±S.D. for six values.
Figure 2A:
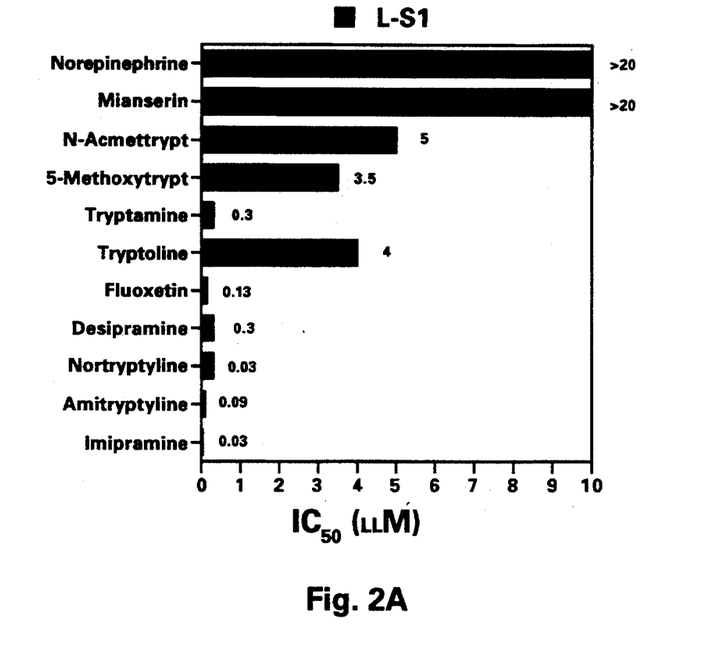
FIG. 2 shows IC$_{50}$ values for (A) L-S1 and (B) L-S2 of inhibitors or 5HT receptor antagonists. Values were derived from plots constructed like those in FIG. 1. The IC$_{50}$ value was defined as the concentration of inhibitor required to produce 50% inhibition when cells were assayed at 0.1 μM [$^3$H]-5HT.
Figure 2B:
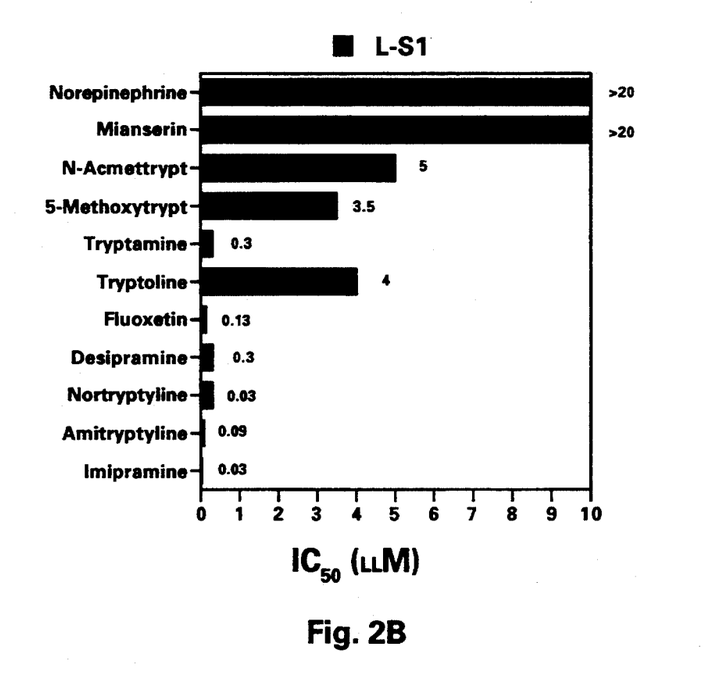

The results showed that the untransformed host cell maintained a relatively constant low level of serotonin uptake. In the transgenic cells, by contrast, of the neurotransmitters or neurotransmitter precursors assayed, only the unlabelled homolog of [$^3$H]5-HT significantly inhibited uptake of labeled 5-HT in both L-S1 and L-S2 cells (FIG. 1). Neither tryptophan, the amino acid precursor of serotonin, nor the amino acid substrates for catecholamine synthesis, phenylalanine and tyrosine, inhibited uptake of 5-HT. With the exception of GABA, other neurotransmitters included in the assay regime share structural similarities with serotonin. However, in the L-S1 and L-S2 cells, none of the catecholamines competed with serotonin transport, suggesting that the system resulting from genetic manipulation is capable of specifically transporting serotonin. In addition, imipramine, a known inhibitor of serotonin uptake, significantly inhibited [$^3$H]5-HT uptake in L-S1 and LS2 cells at 10 μM.

f. Kinetic Analysis of Serotonin Transporters

Kinetic analyses of [$^3$H]-serotonin uptake by L-S1 were performed. Uptake assays were performed on L-S1 and L-M by incubating the cells with [$^3$H]-serotonin at the following concentrations (M): $4 \times 10^{-5}$, $2 \times 10^{-5}$, $10^{-5}$, $5 \times 10^{-6}$, $2 \times 10^{-6}$, $10^{-6}$, $5 \times 10^{-7}$, $2 \times 10^{-7}$ and $10^{-7}$ at 37° C. for 10 minutes. Initial observations had shown that the rate of uptake was linear within this time period. Non-specific activity was determined from parallel assays carried out at 0° C. Initial velocities were calculated in terms of pmol/mg protein/min by subtracting velocity values obtained at 0° C. from those obtained at 37° C.

Michaelis-Menten plots of initial velocities for L-S1 and L-S2 showed discernibly saturable uptake kinetics which are not observed in untransfected L-M cells. Lineweaver-Burk transformation of the kinetic profiles revealed that kinetic data for L-S1 and L-S2 can be fitted by linear regression analysis into lines with discernible x and y axis intercepts, while the linear function of L-M cells gives no y-axis intercept. These observations imply that L-S1 and L-S2 but not L-M cells possess 5-HT uptake systems with well defined kinetic parameters. To further verify the presence of high-affinity uptake systems with definable kinetic parameters, L-S1 and L-S2 were assayed in the presence of excess unlabelled 5-HT. Under these conditions, Lineweaver-Burk plots of velocity profiles shifted in slope toward that of LM cells indicating that excess unlabelled 5-HT significantly inhibited [$^3$H]5-HT uptake by L-S1 and L-S2. Kinetic parameters of 5-HT uptake ($K_m$ and $V_{max}$) are comparable to those determined for other serotonin uptake systems: (L-S1, $K_m = 0.390 \pm 0.096$ μM, $V_{max} = 2.14 \pm 0.55$ pmol/mg/min; L-S2, $K_m = 0.234 \pm 0.027$ μM, $V_{max} = 1.33 \pm 0.13$ pmol/mg/min).

Unlike that in L-S1 and L-S2, the activity associated with L-M cells was unaffected by unlabeled serotonin or imipramine. Residual activity in untransfected fibroblasts probably arose from non-specific diffusion or from the presence of a low-affinity component which was not affected by inhibitors of serotonin uptake. On the other hand, inhibition of 5-HT uptake in L-S1 and L-S2 by unlabeled serotonin and imipramine provides additional supporting evidence for the presence of a system in these cells comparable to that present in synaptosomes and blood platelets.

To determine the mechanism of imipramine in inhibiting 5-HT uptake, L-S2 cells were assayed in the presence of various concentrations of the inhibitor (0, 0.2, and 2 μM). Lineweaver-Burk transformations of the velocity profile showed that while the value of the y-intercept (representing $1/V_{max}$) remained essentially constant, the slope was markedly increased in the presence of higher imipramine concentrations. This observation is consistent with competitive inhibition and suggests that in transfectant cell lines, imipramine and serotonin bind to the same site or overlapping sites on the serotonin transporter. When assays were repeated at lower concentrations of imipramine, (0.0075, 0.02, and 0.1 μM), similar graphical results were obtained from which a $K_i$ with a value of $22.7 \pm 5.2$ nM was calculated. This result compares favorably with that reported for platelets (Humphreys et al., *Molecular Pharmacology* (1988) 33:657–663) and brain synaptosomes (Marcusson et al., *Molecular Pharmacology* (1986) 30:121–128), further demonstrating the remarkable similarities between L-S1 and L-S2 and other systems of 5-HT uptake.

g. Assay of Antidepressants and Other Pharmacological Agents

Several known inhibitors of high-affinity 5-HT uptake systems (including amitriptyline, desipramine, fluoxetine, imipramine, nortriptyline, tryptamine, 5-methoxytryptamine and N-acetyl-5-methoxytryptamine) were assessed in terms of their respective potencies in inhibiting [$^3$H]-5-HT uptake by L-S1 and L-S2 cells. Dilutions of inhibitors were prepared in oxygenated Ringer's buffer so that incubation concentrations varied from 0.005–20 μM depending upon inhibitor potency. Cells were washed as described above and preincubated at 37° C. for 10 minutes before the addition of [$^3$H]5-HT to give an incubation concentration of 0.1 μM. Cells were assayed in the presence of each inhibitor for 40 minutes at 37° C., washed with Ringer's buffer and prepared for counting as previously described. Five confluent wells were assayed at each inhibitor concentration. The $IC_{50}$ value for each inhibitor was determined by plotting the percent activity against the logarithm of inhibitor concentration. Measured levels of uptake in the presence of inhibitors were expressed as the percentage of maximal uptake (100%) in the absence of inhibitor.

Analyses of results obtained from the various inhibitors revealed the presence of both high and low affinity components in both cell lines. These two components became apparent when uptake was measured in the presence of the more potent inhibitors (e.g., imipramine, fluoxetine). The high-affinity component presumably represents Na+ dependent uptake and is most susceptible to inhibitor treatment. A second component, which is essentially nonresponsive to further increases in inhibitor concentration, probably represents temperature dependent, nonspecific diffusion; its activity at 37° C. is only partially accounted for by carrying out parallel incubations at 0° C. (data not presented). Untransfected L-M cells were unaffected by inhibitor treatment which further supports the conclusion that the transporter systems in L-S1 and L-S2 result from expression of transfected human DNA.

The $IC_{50}$ values obtained for the various inhibitors tested are in good agreement with those reported for brain preparations and platelets (Tables II and III). The structure-activity relationship of the tricyclic antidepressants to 5-HT uptake inhibition in L-S1 and L-S2 is consistent with that previously reported, for example, the tertiary amines, imipramine and amitriptyline, are more potent inhibitors of uptake than their desmethyl derivatives, desipramine and nortriptyline. This relationship between structure and inhibitor potency in transgenic cell lines is in contrast to that observed for the norepinephrine uptake system, in which the secondary amines were more potent inhibitors (Iversen, "Uptake Processes for Biogenic Amines in Handbook of Psychopharmacology, 3:381–442 (Eds. Iversen et al.) Plenum Press, Oxford (1975)]. Desipramine, currently being used as an adjunct to initiate abstinence in cocaine addicts (Barnes Science (1988) 241:1029–1030), is a more potent inhibitor of 5-HT uptake in L-S1 and L-S2 than in other systems (Tables II and III).

As a group, the tricyclic antidepressants were the most effective in inhibiting uptake by the transfectant cell lines; however, the nontricyclic antidepressant and serotonin uptake blocker, fluoxetine, also exhibited a high degree of potency and in L-S2 was as effective as imipramine. Tryptoline, a tetrahydro$\beta$carboline which may arise in vivo through condensation of indoleamines and aldehydes (Elliot & Holman, Neuroregulators and Hypothesis of Psychiatric Disorders (Oxford Press, (1976)), was relatively ineffective in inhibiting 5-HT transport.

Assays designed to test the effectiveness of tryptamine and two of its derivatives in inhibiting 5-HT uptake showed that 5-methoxy and N-acetyl-5-methoxy substituents were far less effective than was the parent compound. Furthermore, the transgenic cell lines exhibited greater sensitivity than other systems, yet the rank order of potency was in complete agreement with that of an earlier study in which the same derivatives were used to investigate 5-HT transport inhibition in rat hypothalamic preparations (Horn, J. Neurochem (1973) 12:883–888).

For L-S1 cells, the rank order of inhibitor potencies is imipramine > amitriptyline > fluoxetine > desipramine = nortriptyline > tryptamine > 5-methoxytryptamine > N-acetyl For L-S2, the rank order is similar to that of L-S1 except that fluoxetine is more potent than amitriptyline.

TABLE II
Tricyclic Antidepressants Representative $IC_{50}$ Values

| Inhibitor | Tissue/Synaptosomes/Cells | μM | Reference[1] |
|---|---|---|---|
| Imipramine | Purified Synaptosomes | 0.210 | Wood et al. (1986) |
|  | Synaptosomes | 0.100 | Michael et al. (1987) |
|  |  | 0.760 | Langer et al. (1980) |
|  |  | 0.100 | Whipple et al. (1983) |
|  | Cultured Astrocytes (rat) | 0.140 | Kimelberg (1988) |
|  | Human Platelets | 2.900 | Todrick & Tait (1969) |
|  |  | 0.700 | Paul et al. (1980) |
|  |  | 0.018 | Rehavi et al. (1981) |
|  |  | 0.044 | Segonzac et al. (1985) |
|  | L-S1 | 0.030 |  |
|  | L-S2 | 0.030 |  |
| Amitriptyline | Rat Synaptosomes | 0.300 | Michel et al. (1987) |
|  |  | 0.800 | Kannengieser et al. (1973) |
|  | Cultured Astrocytes (rat) | 0.140 | Kimelberg (1988) |
|  | Human Platelets | 0.023 | Rehavi et al. (1981) |
|  |  | 0.700 | Paul et al. (1980) |
|  | L-S1 | 0.090 |  |
|  | L-S2 | 0.040 |  |
| Desipramine | Ray Synaptosomes | 1.800 | Wood et al. (1986) |
|  |  | 4.780 | Langer et al. (1980) |
|  |  | 0.430 | Stauderman (1986) |
|  |  | 6.000 | Kannengiesser et al. (1973) |
|  | Cultured Astrocytes (rat) | 0.620 | Kimelberg (1988) |
|  | Human Platelets | 9.600 | Todrick & Tait (1969) |
|  |  | 0.160 | Rehavi et al. (1981) |
|  | L-S1 | 0.300 |  |
|  | L-S2 | 0.150 |  |
| Nortriptyline | Rat Synaptosomes | 2.400 | Langer et al. (1980) |
|  |  | 0.500 | Michel et al. (1987) |
|  | Rabbit Platelets | 0.900 | Paul et al. (1980) |
|  | Human Platelets | 2.000 | Paul et al. (1980) |
|  | L-S1 | 0.300 |  |
|  | L-S2 | 1.000 |  |

[1]References
Kannengiesser, M.H. et al., Biochem. Pharmacol. (1973) 22:73804.
Kimelberg, H.K., Neuronal Serotonin (Eds. Osborne and Hamon), (1988) pp 347-365.
Langer, S.Z. et al., Science (1980) 210:1133-1135.
Michel, M.C. et al., Biochem. Pharmacol. (1987) 36:3175-3180.
Paul, S. et al., Life Sciences (1980) 26:953-959.
Rehavi, et al., Biochem. Biophys. Res. Comm. (1981) 99.
Segonzac, A. et al., J. Neurochem. (1985) 45:249-256.
Stauderman, K.A. et al., Brain Research (1985) 330:11-20.
Todrick, a., J. Phar. Pharmaco. (1969) 21:751-762.
Wood, M.D., et al., Neuropharmacology (1986) 25:519-525.

TABLE III
Additional Serotonin Uptake Inhibitors Representative $IC_{50}$ Values

| Inhibitor | Tissue/Synaptosomes/Cells | μM | Reference[1] |
|---|---|---|---|
| Fluoxetine | Rat Synaptosomes (Purified) | 0.290 | Wood et al. (1986) |
|  | Rat Synaptosomes (Crude) | 0.075 | Stauderman & Jones (19867) |
|  |  | 0.560 | Langer et al. (1980) |
|  | Cultured Astrocytes (rat) | 0.023 | Kimelberg (1988) |
|  | Human Platelets | 0.044 | Segonzac (1980) |
|  | L-S1 | 0.130 |  |
|  | L-S2 | 0.040 |  |
| Tryptoline | Rat Synaptosomes | 2.500 | Langer et al. (1984) |
|  | Human Platelets | 3.800 | Segonzac et al. (1985) |
|  | L-S1 | 4.000 |  |
|  | L-S2 | 8.000 |  |
| Tryptamine | Rat Synaptosomes | 2.800 | Horn (1973) |
|  | Human Platelets | 2.700 | Stacey (1961) |

TABLE III-continued

Additional Serotonin Uptake Inhibitors Representative IC$_{50}$ Values

| Inhibitor | Tissue/Synaptosomes/Cells | μM | Reference[1] |
|---|---|---|---|
| | L-S1 | 0.130 | |
| | L-S2 | 0.900 | |
| 5-methoxy-tryptamine | Rat Synaptosomes | 25.00 | Horn (1973) |
| | L-S1 | 3.500 | |
| | L-S2 | 1.500 | |
| N-Acetyl-5-methoxy-tryptamine | Rat Synaptosomes | 66.00 | Horn (1973) |
| | L-S1 | 5.000 | |
| | L-S2 | 9.000 | |
| Mianserin | Rat Synaptosomes | 8.000 | Green & Constain (1981) |
| | Cultured Astrocytes (rat) | 4.900 | |
| | L-S1 | >20.00 | |
| | L-S2 | >20.00 | |
| Norepinephrine | Rat Synaptosomes | >10.00 | Wood et al. |
| | L-S1 | >20.00 | |
| | L-S2 | >20.00 | |
| 5-HT (Serotonin) | Rat Synaptosomes | 0.150 | Wood et al. (1986) |
| | L-S2 | 3.500 | |

[1]References
Green, A.R. et al., Pharmacology and Biochemistry of Psychiatric Disorders (1981) pp 71-88.
Horn, A.S., J. Neurochemistry, (1973) 12:883-888.
Kimelberg, H.K., Neuronal Serotonin (Eds. Osborne and Hamon), (1988) pp 347-365.
Langer, S.Z. et al., Science (1980) 210:1133-1135.
Segonzac, A. et al., J. Neurochem. (1985) 45:249-256.
Stacey, R.A., Brit. J. Pharmacol. (1973) 22:73-84.
Stauderman, K.A. et al., Brain Research (1985) 330:11-20.
Wood, M.D., et al., Neuropharmacology (1986) 25:519-525.

Mianserin, a tetracyclic antidepressant which acts postsynaptically and is an antagonist of 5-HT$_2$ receptors (Peroutka, "Functional Correlates of Central 5-HT Binding Sites" in *Neuronal Serotonin* pp. 347-365 (Eds. Osborne and Hamon) (J. Wiley & Sons, N.Y.)), had no effect on uptake of 5-HT by either cell line even at a concentration of 20 μM. When compared to tricyclic antidepressants, much higher concentrations of mianserin were required to inhibit 5-HT uptake by 50% in both rat astrocytes cultured from cerebral cortex (Kimbelberg, "Serotonin Uptake in Astrocytes and Its Implications" in *Neuronal Serotonin* (Eds. Osborne and Hamon) [J. Wiley & Sons, N.Y. (1988)], as well as in rat synaptosomes (Green & Constain, in *Pharmacology and Biochemistry of Psychiatric Disorders* (J. Wiley & Sons, NY (1981), pp. 71-88). The ineffectiveness of mianserin in blocking uptake in L-S1 and L-S2 suggests that the cell-associated uptake activity arises from an active uptake system in the plasma membrane and does not occur by receptor-mediated binding to the cell surface. This suggestion is substantiated by the observation that when a wide array of 5-HT receptor agonists and antagonists were tested, they exerted no effect on specific, imipramine-displaceable [$^3$H]-5-HT binding to intact L-S1 and L-S2 cells, as well as [$^3$H]-5-HT transport into these cells.

h. Genomic Analysis of Transgenic Cells Comprising Serotonin Transporters

Genomic blotting analyses with a human Alu sequence probe indicated that L-S1 cells contained integrated human DNA, as indicated by discrete hybridizing DNA fragments within an extensive smear pattern. In contrast, no discernible hybridizing signal was observed with L-M cells. By comparison of the overall hybridizing strength observed for L-S1 DNA with that of known quantities of human genomic DNA, a conservative estimate is that L-S1 cells contain over $10^6$ bps of stably integrated human DNA. Similar analyses revealed that L-S2 cells contain about $3 \times 10^4$ bp of human DNA per genome.

The presence of human DNA in both cell lines supports the contention that human 5HT transporter gene(s) integrated into the cell genome and is manifested in the expression of a high-affinity serotonin uptake mechanism.

EXAMPLE III

Transgenic Cells Containing a Glycine Transporter a. Screening for Glycine Uptake

The transfectants obtained as described in Example I were screened for uptake of [$^3$H] glycine. The [$^3$H] glycine-uptake assay was performed in 96-well plates by incubating each well with 50 μl of oxygenated Ringer's buffer (128 mM NaCl, 5.2 mMKCl, 2.1 mM CaCl$_2$, 2.9 mM MgSO$_4$, 5 mM glucose, 10 mM HEPES, pH 7.4), supplemented with 1 mM each of alanine, serine, proline and 0.1 μM [$^3$H]glycine (New England Nuclear, 43.5 Ci/mmol). The incubation was conducted for 40 min at 37° C. Each well was washed three times at room temperature with excess Ringer's buffer and then incubated with 50 μl of alkaline phosphatase buffer (100 mM Tris, pH 9.5, 100 mM NaCl, 10 mMMgCl$_2$, 20 μg/ml saponin, 3.2 mg/ml p-nitrophenyl phosphate) for 1-2 hours at 37° C. The phosphatase assay was used as a relative assessment of cell number, and used to normalize the level of [$^3$H]glycine associated with each well as described above. The phosphatase reading for each assayed well was plotted versus its corresponding level of [$^3$H]glycine-retention. Cells identified as high responders were cloned and reassayed, as described above in Example II for the serotonin transporter. Since all cells possess a low-affinity glycine uptake mechanism for metabolic purposes which is diminished by inclusion of 1 mM alanine, proline and serine in all assays, only the wells that contained high-responding cells were expanded. These wells were reassayed and ultimately yielded eight clones that manifested relatively high [3H]glycine-accumulation levels as compared to L-M cells. One of these clones, L-GLY2, was used for further analysis. This clone arose from the highest-responding well in the initial screening.

b. Temperature and Ion Dependence of Glycine Transporter

(i) Sodium-dependence

Sodium dependence of [$^3$H] glycine-uptake was tested by iso-osmotically replacing the assay Ringer's NaCl concentration to variable extents with sucrose, as described above in Example II. The resulting iso-osmotic series of Ringer's buffers were each used in uptake assays for L-GLY2 and L-M cells. Each assay was conducted with 0.1 μM [$^3$H]-glycine in the presence of 1 mM alanine, proline and serine at 37° C. for 40 minutes. The amount of protein in each assayed well was determined via the BCA method (as mentioned in Example II) and used to normalize the level of [$^3$H]-glycine accumulation in the test wells.

When the concentration of NaCl in the assaying Ringer's solution was iso-osmotically replaced by sucrose to varying extents, LGLY2 cells exhibited an almost linear dependence on extracellular [Na+] for [$^3$H]glycine uptake. L-M cells likewise demonstrated near-linear dependence on extracellular [Na+], but this was not nearly as discernable as that of L-GLY2 because the maximal level of [$^3$H]glycine uptake by L-M cells was significantly less than that of L-GLY2 cells. Clearly, L-GLY2 cells exhibited a [H] glycine-uptake mechanism that is sodium-dependent. However, the relatively smaller uptake activities associated with L-M cells also seemed to have a sodium-dependent component.

(ii) Temperature-dependence

The temperature dependence of [$^3$H] glycine uptake was determined by assaying both L-GLY2 and L-M cells at 37° C. versus 0° C. (on ice). Each assay was conducted between 0 and 40 min., and [$^3$H]glycine accumulation at several time-points therein was quantitated and normalized by corresponding protein contents. At 37° C., [$^3$H]-glycine-accumulation by L-GLY2 cells increased almost linearly with incubation times up to 40 minutes. The transport of [$^3$H] glycine by L-M cells at 37° C. was significantly less than that of L-GLY2 cells, but nonetheless distinct from uptake activities at 0° C. Thus, while varying in magnitude, both L-GLY2 and L-M cells exhibit temperature-dependence in [$^3$H] glycine uptake.

c. Screening for Specificity of Glycine Transporter

L-GLY2 and L-M cells were assayed for the uptake of [$^3$H] glycine (0.1 μM) in the presence or absence of competing, unlabelled amino acids or neurotransmitters. Each competing ligand was present in 1000-fold molar excess (100 μM) of the [$^3$H] glycine. The competing neurotransmitters used included serotonin, dopamine and γ-aminobutyric acid; the competing amino acids used included tryptophan, tyrosine, glutamine, valine, cysteine, glutamate and lysine. The assays were performed at 37° C. for 40 minutes. Alanine, proline and serine, each at 1 mM, was added to the Ringer's buffer for all assays.

In the presence of 1000-fold molar excess of unlabelled neurotransmitter or amino acids, transport of [$^3$H] glycine into L-GLY2 cells exhibited no change except in the presence of unlabelled glycine. This indicated that the glycine-uptake mechanism in L-GLY2 was specific with regard to its substrate. Uptake of [$^3$H] glycine into L-M cells was not significantly inhibited by any competing ligand, including unlabelled glycine. These results suggested that the uptake mechanism in L-GLY2 cells is saturable since a 1000-fold excess of glycine reduced [$^3$H] glycine transport into L-GLY2 cells to the same level as that of L-M cells. Thus, L-GLY2 cells are expressing a [$^3$H] glycine-uptake mechanism which is neurotransmitter- and amino acid-specific, competible and absent from L-M cells.

d. Kinetic Analysis of Glycine Transporter

Various concentrations of [$^3$H] glycine (ranging from 50 nM to 5 μM) were used to assay L-GLY2 and L-M cells for 10 minutes because within this time frame the velocity of [$^3$H] glycine uptake by L-GLY2 appeared linear at both 37° C. (total uptake) and 0° C. (nonspecific uptake). At each concentration of [$^3$H] glycine used, both uptake levels were converted to picomole-equivalents of [$^3$H] glycine, then normalized by both length of assay and corresponding protein contents to arrive at the uptake velocity values. The nonspecific uptake velocity was then subtracted from the total uptake velocity to yield the specific uptake velocity. The specific uptake velocities and their corresponding [$^3$H] glycine concentrations were analyzed by both Michaelis-Menten and Lineweaver-Burk transformations of the resulting kinetic profiles. For both analyses, data-points were fitted to either linear or logarithmic functions by computerized algorithms.

The resulting Michaelis-Menten plot indicated that the kinetic profile of L-GLY2 was curvilinear (concave downward). This implied that the [$^3$H] glycine-uptake observed for L-GLY2 cells was a kinetically saturable event. L-M, on the other hand, yielded a linear kinetic relationship that was quite diminutive in magnitude when compared with that of L-GLY2. L-M cells exhibited nonsaturable kinetics within the range of [$^3$H] glycine concentrations employed. Lineweaver-Burk transformations of the kinetic data resulted in linear relationships for transport of glycine in both L-GLY2 and L-M cells. The line corresponding to L-GLY2 cells has a discernable positive ordinate-intercept and a negative abscissa-intercept. In contrast, the line representing L-M cells had neither. This was a clear demonstration that L-GLY2 cells exhibited a discernable [$^3$H] glycine-uptake mechanism which was saturable and of high-affinity. This transporter mechanism for [$^3$H] glycine was absent from L-M cells. Within the concentration range of [$^3$H] glycine which was assayed, L-M cells exhibited neither discernable affinity nor capacity for glycine transport.

The Lineweaver-Burk plot for L-GLY2 yielded an apparent $K_m$ of $1.50 \pm 0.20 \times 10^{-6}$M and a $V_{max}$ of $10.19 \pm 3.32$ pmol/min/mg protein. As shown in Table IV. These values are comparable to published values for high-affinity glycine uptake in the CNS (Chin & Lam (1980) *J. Physiol.* 308:185–195; Voaden, Marshall & Murani (1974) *Brain Res.* 67:115–132; Muller & Snyder (1978) *Brain Res.* 143:487–498; Mayor, Marvizon, Aragon, Gimenez & Valdivieso (1981) *Biochem. J.* 198:535–541; Hardy, Barton, Lofdahl, Cheetham, Johnston & Dodd (1986) *J. Neurochem.* 47:460–467; Zafra & Gimenez (1986) *Brain Res.* 397:108–116; Debler & Lajtha (1987) *J. Neurochem.* 48:1851–1856; Yorek, Dunlap & Ginsberg (1987) *J. Biol. Chem.* 262:10986–10993; Hendrickson, Koontz, Pourcho, Sarthy & Goebel (1988) *J. Comp. Neurol.* 273:473–487) and definitively establish L-GLY2 cells as possessing a high-affinity glycine uptake mechanism which is absent from L-M cells.

TABLE IV

| TISSUE/ SYNAPTOSOME/CELL | $K_m$ (μM) | $V_{max}$ (pmol/mg/min) |
|---|---|---|
| L-GLY2 | 1.50 ± 0.20 | 10.19 ± 3.32 |
| Tissue: | | |
| goldfish retina | 8.08 ± 0.70 | 8.71 ± 0.54 |
| monkey retina | 2.50 ± 0.90 | 3.30 ± 1.60 |
| frog retina | >4.70 | |
| Membrane Preparations: | | |
| human brain (post-mortem) | 35 ± 19 | 55 ± 25 |
| C6 glioblastoma | 100 | |
| frog brain | 24.80 ± 1.40 | 1.14 ± 0.06 |
| frog spinal cord | 29.00 ± 0.70 | 1.52 ± 0.03 |
| rat brain | 34.00 ± 1.30 | 0.48 ± 0.07 |
| rat spinal cord | 46.50 ± 1.60 | 1.43 ± 0.02 |
| chicken brain | 37.00 ± 2.00 | 0.32 ± 0.01 |
| chicken spinal cord | 41.80 ± 1.00 | 0.65 ± 0.02 |
| mouse cerebral cortex | 15.20 ± 2.00 | 340 ± 70 |
| mouse pons-medulla-spinal cord | 27.60 ± 2.60 | 3100 ± 100 |
| Cell: | | |
| Y79 retinoblastoma | 24.40 ± 2.60 | 138.40 ± 12.40 |

In another kinetic analysis, the assaying concentrations of [$^3$H] glycine were increased to between 1 μM and 100 μM. The resulting kinetic profiles for both L-GLY2 and L-M cells were saturable, with L-GLY2 cells exhibiting slightly higher uptake velocities than L-M cells. Lineweaver-Burk transformations of this set of uptake data yielded two overlapping lines having comparable intercepts on both axes. The affinity and capacity measured for these uptake events were comparable to those of am±no acid uptake systems that are present in all cells (Oxender & Christensen (1963) *J. Cell Biol.* 238:3686–3699; Revsin & Morrow (1976) *Exp. Cell Res.* 100:95–103; Sepulveda & Smith (1978) *J. Physiol.* 282:73–90). Thus, while both L-GLY2 and L-M cells possess low affinity amino acid uptake mechanisms, only L-GLY2 cells in addition manifested a distinct, high-affinity glycine-uptake mechanism.

e. Genomic Analysis of Transgenic Cells Comprising The Glycine Transporter

Genomic DNA was extracted from L-GLY2 cells, digested to completion by restriction endonucleases BamHI and EcoRI (New England BioLabs), and electro-phoretically separated on a 0.8% agarose gel. Following depurination and denaturation, the DNA fragments were absorbed onto Nytran filters (Schleicher & Schuell, Inc.) and hybridized with the 300 bp human Alu probe isolated by BamHI-digestion of pBLUR-8 (Jelinek, et al., (1980) *Proc. Natl. Acad. Sci. USA* 77:1398–1402). The probing Alu insert was labelled by random-priming (Feinberg & Vogelstein (1983) *Anal. Biochem.* 132:6–13) with [α-$^{32}$P]dCTP (New England Nuclear, 3000 Ci/mmol).

Both the hybridization and subsequent washings were performed at very high stringencies, and the resulting blot exposed at −70° C. to Kodak XAR5 film in the presence of an intensifying screen (DuPont). The resulting autoradiogram illustrated the presence of human Alu sequences within the L-GLY2 cells, showing that integration of human DNA into the L-M genome had occurred during the initial transfection (described in Example I). EcoRI-digestion of L-GLY2 DNA resulted in two closely-spaced hybridizing bands, while BamHI-digestion resulted in three discernable bands. Each of these digestions indicated that the hybridizing bands comprised approximately $2 \times 10^4$ bp of human DNA per L-GLY2 genome. Parallel hybridization of L-M genomic DNA revealed no dicernable hybridizing signal. This is consistent with the Alu sequences being restricted to primate species (Houck et al., *J. Mol. Biol.* (1979) 132:289–306). The correlation between the presence of a high-affinity glycine-uptake mechanism and the integration of human DNA into the genome of L-GLY2 cells indicated that the high-affinity glycine-uptake mechanism in L-GLY2 resulted from the expression of stably-integrated human gene(s) encoding the glycine transporter.

EXAMPLE IV

Transgenic Cells Containing a Dopamine Transporter a. Screening of Transfectants for [$^3$H-Dopamine Uptake Cell transfectants, obtained as described in Example I, were trypsinized and replated into separate sets of 96-well culture plates for assay and cell-stocks. During the initial screening, the entire bank of transfectants was assayed for [$^3$H] dopamine uptake. At the time of assay, the culture medium from each well was removed, the cells rinsed with 200 μl of oxygenated Ringer's solution (128 mM NaCl, 5.2 mM KCl, 2.1 mM CaCl$_2$, 2.9 mM MgSO$_4$ 5 mM glucose, 10 mM HEPES, p 7.4, supplemented with 0.5 mM ascorbate, 10 μM pargyline) and then incubated for 40 minutes at 37° C. with 50 μl Ringer's solution plus 0.1 μM [$^3$H] dopamine (New England Nuclear; 40 Ci/mmol). The incubation mixture was then removed and the cell plates were placed on ice for 30 minutes before three 2-minute washings with 100 μl ice-cold isotonic NaCl. Each well was then incubated with 50 μl of alkaline phosphatase assay mixture (100 mM Tris, pH 9.5, 100 mM NaCl, 10 mM MgCl$_2$, 20 μg/ml saponin, 3.2 mg/ml p-nitrophenyl phosphate), as described in Examples I and II above. Then, 100 μl of 1% SDS was added per well. The lysed content of each well was quantitated by liquid scinfillation spectrometry.

The wells identified as containing relatively high [$^3$H]-dopamine cpm, when normalized by the phosphatase assay, were then expanded from stock plates and rescreened. Additionally, these secondary clones were rigorously assayed with 0.1 μM [$^3$H]-dopamine alone or following a preincubation period of 10 minutes with 10 μM unlabelled dopamine or 125 μM benztropine, to confirm the presence of a specific dopamine uptake mechanism.

Wells which consistently exhibited high dopamine uptake and were inhibited by both unlabelled dopamine and benztropine were used to generate single cell cultures. To ensure representative populations of monoclones in sufficient numbers, at least four 96 well plates of monoclones were generated from each secondary well. An 80% success rate for generation of single cell cultures was attained by plating an average of 75 cells per 96 well plate.

After initial plating of individual cells, each well was carefully monitored for the presence of only a single clone. Wells were monitored at weekly intervals and only those clones which had attained confluence were trypsinized and replated for assays. This was a necessary step to obviate the potential lethal effects of premature trypsinization. Two clones (L-D1 and L-D2) showing specific uptake of [³H]-dopamine were identified by the screening procedure.

b. Rate and Kinetics of Dopamine Uptake

Rates of dopamine uptake by identified transgenic clones and untransfected cells were determined by incubation of the cells for selected intervals from 0 to 40 minutes at 37° C. Uptake rates were simultaneously determined with 0.1 µM [³H]-dopamine alone or following preincubation with 10 µM unlabelled dopamine or 125 µM benztropine. For L-D2, uptake was linear from zero to 10 minutes after addition of [³H]-dopamine. Kinetic analyses, using concentrations ranging from $7.5 \times 10^{-7}$ to $1.0 \times 10^{-5}$M [³H]dopamine were carried out for 10 minutes at both 37° C. and 0° C. (on ice). After 10 minutes, the Ringer's solution containing [³H]-dopamine was removed, and the cells were allowed to cool on ice for 30 minutes. Following three 2-minute washings with ice-cold isotonic NaCl, the cells were dissolved in 150 µl of 1% SDS. Cell-associated radioactivity in L-D2 cells measured at 0° C. was significantly lower than that measured at 37° C.

The initial uptake velocity was determined by subtracting initial uptake velocity at 0° C. from that measured at 37° C., each based on the specific activity of the [³H] label, incubation time, and protein concentration (determined by the method of Lowry; Lowry, Rosebrough, Farr Randall *J. Biol. Chem.* (1961) 193:256. Kinetic data were expressed in the form of a Michaelis-Menten plot or a Lineweaver-Burk plot (of inverse initial velocities versus inverse concentrations) using computerized curve-fitting algorithms.

c. Sodium Ion Dependence of Dopamine Transporters

Sodium ion dependence will be determined by incubating L-d1, L-D2 and L-M cells at various concentrations of Na+ (0 to 128 mM) in oxygenated Ringer's solution. Sodium ion will be isosmotically replaced by an appropriate concentration of sucrose. For total replacement of Na+, 256 mM sucrose will be utilized.

d. Autoradiographic Analysis

Untransfected cells and L-D2 cells will be plated in 100 mm dishes and assayed for uptake with 0.1 µM [³H]-dopamine for 20 minutes at 37° C. Following three washes with ice cold isotonic NaCl, cells in each plate will be transferred to microcentrifuge tubes, and will be resuspended and pelleted twice in cold isotonic NaCl. The cell pellets will be fixed with paraformaldehyde (at 4° C. for 16 hours) before being embedded in EPONaryldite. Ultramicrotome sections of 1 µm thickness will be obtained for each cell pellet and coated with TB-2 nuclear tract emulsion (Polyscience). The slides will be maintained in the dark at 4° C. for up to six weeks before development. The presence of silver grains (representing [³H] dopamine) in intracellular domains will be determined at the light microscopic level.

e. Genomic Blotting Analysis

Genomic DNAs for each cell line will be purified by SDS-phenol extraction. Each sample will be digested with excess restriction endonucleases (New England Biolabs) and electrophoresed through agarose gels along with size markers (Hind III/EcoRI digested λ DNA). DNA samples will be transferred from gels orthogonally onto Nitran filters (Schleicher & Schuell). The human Alu sequence insert will be isolated by BamHI-digestion of pBLUR-8 (Jelinek et al., *Proc. Nat'l. Acad. Sci.* USA (1980) 77:1398) labelled with [32Pl-dCTP (New England Nuclear, 3000 Ci/mmol) by random priming (Feinberg & Vogelstein, *Anal. Biochem* (1983) 132:6) and used as a hybridization probe. Both the hybridizations and subsequent washings will be performed under very stringent conditions and the resulting blots exposed to Kodak XAR-S films at −70° C. with intensifying screens.

f. Screening for Agonists and Antagonists of Dopamine Uptake

A number of centrally-acting drugs, including anti-Parkinsonian agents, anti-histamines, tricyclic antidepressants and phenothiazine, inhibit catecholamine uptake by synaptosomes prepared from various areas of rat brain (Horn, et al., *Molec. Pharmacol.* (1971) 7:66). Many of these drugs act as noncompetitive, reversible inhibitors of dopamine uptake by dopaminergic neurons in the corpus striatum where dopamine is the predominant catecholamine. For a transporter, the $IC_{50}$ value is the concentration of inhibitor required to inhibit uptake by 50% as compared to controls without inhibitor. $IC_{50}$ values will be determined for at least four known inhibitors of dopamine uptake: benztropine, diphenyl-pyraline, chlorocyclozine, and nortriptyline, using log probit plots in which the log of percent inhibition of uptake is plotted against inhibitor concentration. The percentage inhibition of uptake will be determined by using at least three different concentrations of inhibitor ranging from $10^{-7}$ to $10^{-5}$M by assaying L-D1 and L-D2 cells at 0.1 µM [³H]-dopamine and at 37° C. Nonspecific or low affinity binding will be determined by carrying out simultaneous incubations at 0° C. Untransfected L-M cells will be used as negative controls. The $IC_{50}$ values obtained from these studies will be compared to those reported for striatal dopaminergic neurons (Horn et al., *Molecul. Pharmacol.* (1971) 7:66). These data should indicate the extent to which the two transgenic clones mimic the pharmacological characteristics of systems known to possess a high-affinity dopamine transport mechanism.

g. Screening for Specificity of Dopamine Transporter

The specificity of L-D1 and L-D2 cells for dopamine transport will be determined via competition assays involving selected amino acids bearing structural homology to dopamine (tyrosine, tryptophan, phenylalanine), amino acid derivatives with structural resemblance (tyramine, tryptamine and L-dopa), and other neurotransmitters (including γ-aminobutyric acid serotonin, epinephrine and norepinephrine). Incubations at 37° C. will be performed utilizing 0.1 µM [³H] dopamine and 10 µM concentrations of each of the potential ligands listed for predetermined periods of time optimum for these studies. All data will be normalized for protein concentration. Untransfected L-M cells will be used as negative controls. Incubations will be carried out at 37° C. and all data will be normalized for protein concentration.

EXAMPLE V

Transgenic Cells Containing a High-Affinity L-glutamate Transporter

A clonal cell line, L-Glu1, has been identified for its higher capacity to transport and internalize L-[³H] glutamate ([³H]Glu) as compared to untransfected L-M cells. L-Glu 1 exhibits temperature dependence in terms of its Glu-uptake activities, since at 37° C. (physiological temperature) it is much more active than at 0° C. (on ice). Further, this cell line also shows increasing accumulation of [$^3$H] Glu with increasing incubation time in the uptake assay.

Both L-Glul and L-M cells were assessed for their kinetic properties of [$^3$H] Glu uptake, and the results were analyzed by fitting to Michaelis-Menten kinetics. This was done by incubating cells with differing concentrations of [$^3$H] Glu (ranging from 0.05 to 2 μM) for 10 minutes, at both 37° C. and 0° C. The amount of [$^3$H] Glu retained by the cells following incubation was then quantitated and converted (using the manufacturer's specific activity for [$^3$H] Glu to the corresponding picomole-equivalent of the radioligand, for each concentration of radioligand at each temperature. Then, the pmol value is normalized by the length of incubation and the amount of protein corresponding to the number of cells assayed. The resulting value, expressed in units of pmol/min/mg protein, is the initial velocity value for each concentration of [$^3$H] Glu at each temperature. The initial velocity measured at 37° C. represents total initial velocity; the initial velocity measured at 0° C. represents nonspecific initial velocity. The difference between these two velocity values is then the specific initial velocity, denoted by "V", for each concentration of [$^3$H] Glu. When the V-inverse of each cell line is plotted against the concentration-inverse of [$^3$H] Glu for both L-Glul and L-M cells, both sets of data can be best described by straight lines (generated by linear regression).

The line representing L-M cells' uptake kinetics show a positive x-intercept with no positive y-intercept, indicating that L-M cells have no definable [$^3$H] Glu uptake system within these concentrations of [$^3$H] Glu. L-Glul cells, on the other hand, have a positive y-intercept and a negative x-intercept in the double-reciprocal plot, indicating that within these [$^3$H] Glu concentrations an uptake system can be defined in this cell line.

By inverting each of the axes-intercept values for L-Glul's double reciprocal plot, a mean $K_m$ of 2.1 μM and a mean $V_{max}$ of 22.8 pmol/min/mg was obtained. The $K_m$ value for this transport system is definitely lower than those of the ubiquitous amino acid transport systems (characterized by $K_m$ values in the millimolar range), and therefore qualifies this Glu transport system as being one of high-affinity. Further, this $K_m$ value is quite comparable to the $K_m$ values of high-affinity Glu uptake as measured in animal and human brain homogenates (Hertz et al., 1978; Wheeler & Hollingsworth, 1978; Mangano & Schwarcz, 1981; Drejer et al., 1982; Ferkany & Coyle, 1986; Zaczek et al., 1987; Dodd et al., 1989), cultured neurons and glia (Schousboe et al., 1977; Campbell & Shank, 1978; Hertz; et al., 1978; Baetge et al., 1979; Stallcup et al., 1979; Wanewski & Martin, 1984; Nilsson et al., 1989), retina and peripheral nervous tissue (Whille & Neal, 1976; Hertz et al., 1978) as well as blood platelets (Mangano & Schwarcz, 1981). This indicates that the L-Glul cell line possesses a high-affinity L-L-glutamate uptake system. This system is absent in untransfected L-M cells. The high-affinity L-glutamate uptake system in the L-Glul cell line correlates with the transfection of total human DNA into L-M cells and presumably arose due to integration into, and subsequent expression of a human L-glutamate transporter gene in, the mouse genome.

The observation of high-affinity L-glutamate transport activity in [$^3$H] Glu is impingent upon the [$^3$H] Glu concentration being between 0.05 and 2 μM. When the ligand concentration is increased to near millimolar range, the kinetic profiles of L-glutamate uptake by L-Glul and L-M cells become indistinguishable. In that case, both cell lines exhibit the same double reciprocal plot with definable $K_m$ and $V_{max}$. This is due to the fact that higher [H]-Glu concentrations engage the low-affinity amino acid transport systems common to both cell types and thereby obscure the presence of an additional high-affinity uptake mechanism in L-Glul cells. Indeed, the observed $K_m$ of glutamate transport for both cell lines (when measured with near-millimolar concentrations of [$^3$H]-Glu) is above 1 mM.

The high-affinity L-glutamate transport system was further characterized as follows:

(a) Neurotransmitter specificity.

When L-Glul cells were assessed for uptake of [$^3$H] Glu in the presence of various unlabelled neurotransmitters (including D- and L-aspartate, cysteic acid, dopamine, L-glutamate, norepinephrine, serotonin and taurine), only unlabelled L-glutamate seems to mediate some inhibition of the radioligand uptake. This suggests that the high-affinity uptake system in L-Glul cells is indeed specific for L-glutamate, and will not recognize any other neurotransmitter. The surprising finding here is that D- and L-aspartate do not inhibit this high-affinity system. This implies that L-Glul's high-affinity transport system is distinct from the glutamate/aspartate cotransporter thought to be present in the CNS.

(b) Sodium dependence.

The NaCl component in the incubating Ringer's buffer was replaced by chloride salts of various monovalent cations (e.g. LiCl, KCl, RbCl, CsCl and choline chloride). Virtually all of the substitutions of Na+ (except Li+) resulted in diminished uptake of [$^3$H] Glu. This suggests that the high-affinity L-glutamate transport system in L-Glul cells is sodium dependent, and that Li+ is capable of substituting for Na+ in facilitating L-glutamate uptake.

(c) Chloride dependence.

Akin to the sodium dependence study, various sodium salts of monovalent anions were substituted for NaCl in the Ringer's buffer. As shown in FIG. Z, all chloride-substitutions resulted in diminished uptake of [$^3$H] Glu. Thus, the high-affinity transport system in L-Glul is also chloride dependent.

(d) Pharmacological distinction from excitatory amino acid receptor subtypes.

Various drugs specific for excitatory amino acid (EAA) receptor subtypes were assessed for their effects on [$^3$H] Glu uptake by L-Glul cells. While quisqualate was a potent inhibitor of this high-affinity uptake system, D-amino-3-hydroxy-5-methyl-4-isoxazonepropionic acid (AHMIP) (an agonist for the quisqualate subtype of EAA receptors) had no inhibitory effect. This implies that the observed quisqualate inhibition is unrelated to the presence of quisqualate receptors, and therefore more likely represents a direct inhibition on the high-affinity L-glutamate transport system in L-Glul cells. Agents specific for the N-methyl-D-aspartic acid (NMDA)-subtype of EAA receptors (including NMDA, 2-amino-5-phosphonovaleric acid (APV), methyl-glutamylphosphonic acid (MGPA), γ-D-glutamulaminoethyl sulfonate (GAMS), D-homocysteic acid and ibotenic acid) were all without effect. Similarly, 2-amino-4-phosphonobutyric acid (AP4) (ligand for another EAA receptor subtype was without effect as was kainic acid (representative ligand for yet another known subclass of EAA receptors). Thus, the high-affinity glutamate transport system in L-Glu1 cells seems to be unrelated to any of the four major subclasses of EAA receptor subtypes.

(e) Distinction from glutamate/aspartate co-transporter.

The inability of L-aspartate to inhibit this transport system suggested that this system is distinct from the glutamate/aspartate co-transporter found in glutamatergic neurons in the CNS. To further verify this point, APP and cysteine sulfinate (both known to inhibit the glutamate/aspartate co-transport system) were tested and found to have no effect on [$^3$H] Glu uptake by L-Glu1 cells.

These characteristics collectively indicate that, following transfection of human DNA into L-M cells, a high-affinity transport system has been obtained in L-Glu1 cells. This transport system is relatively specific for L-glutamate. Further, this system is dependent on the extracellular presence of both sodium and chloride ions, but distinct from the sodium-dependent glutamate/aspartate transport system found in glutamatergic neurons in the CNS. While this transport system in L-Glu1 is sensitive to quisqualate, this sensitivity is not mediated by the quisqualate-subtype of EAA receptors. Additionally, the NMDA and AP4 receptor-subtypes are not involved in the function of this glutamate transport system. Thus, gene transfer has yielded a clonal, transfectant cell line that expresses a novel, high-affinity transport system specific only for L-glutamate.

EXAMPLE VI

Transgenic Cells Containing a High-Affinity γ-aminobutyric Acid (GABA) Transporter A clonal, transfectant cell line (L-GAB1) was identified based upon its higher capacity to transport and internalize [$^3$H] GABA than untransfected L-M cells. Using concentrations of [$^3$H] GABA ranging from 2 to 500 μM, the kinetic profile of GABA uptake was determined for both L-GAB1 and L-M cells. The initial velocity of GABA uptake was measured and plotted against the corresponding [$^3$H] GABA concentration for both cell lines. Both cell lines exhibit saturable kinetic profiles, indicating the presence, in both cell lines, of specific GABA uptake mechanisms; GABA uptake activity in L-GAB1 cells being higher than that of L-M cells. The velocity profile for L-GAB1 cells was subtracted by that of L-M cells, and the resulting data used for a double-reciprocal plot of velocity-$^1$ against GABA concentration-$^1$. The velocity profile for L-M cells was also transformed into a double-reciprocal plot. Both transformed velocity profiles fit linear relationships with discernable positive y-intercepts and negative x-intercepts. This indicates that both cell lines indeed possess GABA uptake mechanisms with definable affinity ($K_m$) and capacity ($V_{max}$) characteristics. The uptake mechanism in L-M cells is also present in L-GAB1 cells, but not vice versa.

From these kinetic transformations the following transport characteristics were calculated: for L-M and L-GAB1 cells, transport $K_m = 697$ μM, transport $V_{max} = 2.1$ pmol/min/mg protein; for the additional component in L-GAB1 cells, transport $K_m = 110$ μM, transport $V_{max} = 2.4$ pmol/min/mg protein. Since the affinity-value for the GABA transport system present in both cell lines is above 500 μM and therefore more akin to that of low-affinity amino acid transport systems (Martin, 1976; Krogsgaard-Larsen, 1980), we conclude that this transport system is of the low-affinity class and quite possibly one of the known amino acid transport systems that does not discriminate GABA from amino acids.

The affinity-value for the additional GABA transport component in L-GAB1 cells, because it is much lower than the $K_m$ of amino acid transport systems, qualifies as a high-affinity mechanism, but is of lower affinity than most of the high-affinity GABA transport systems previously characterized in the CNS. These are generally lower than 25 μM (Kanner, 1978; Krogsgaard-Larsen, 1980; Lam et al., 1980; Dodd et al., 1989; Kanner & Bendahan, 1990). However, GABA transport mechanisms in the CNS with $K_m$ values in the 50–100 μM range have been reported previously (Iversen & Kravitz, 1968; Levi, 1970; Cohen & Lajtha, 1972; Snodgrass & Iversen, 1974).

Further analyses of this high-affinity GABA transport mechanism in L-GAB1 cells revealed that it is both sodium- and chloride-dependent. When the composition of the incubating Ringer's buffer was altered by substituting sodium chloride individually with various chloride salts of monovalent cations (e.g. lithium chloride, potassium chloride, rubidium chloride, cesium chloride and choline chloride), diminished uptake of [$^3$H] GABA by L-GAB1 cells was observed. Thus this uptake system requires the extracellular presence of sodium ions. Similar substitutions of the NaCl content in the Ringer's composition, using various sodium salts of monovalent anions (e.g. sodium fluoride, sodium isethionate, sodium azide), also resulted in diminished uptake of [$^3$H] GABA by L-GAB1 cells. This is a clear indication of the chloride-dependence of this uptake system. The combination of both sodium- and chloride-dependences for this transport system is consistent with both ion-dependences demonstrated for high-affinity GABA uptake systems in the CNS (Krogsgaard-Larsen, 1980; Pastuszko et al., 1982; Radian & Kanner, 1983; Liron et al., 1988; Dodd et al., 1989).

Several known inhibitors of high-affinity GABA uptake were used to examine their efficacies in inhibiting [$^3$H] GABA uptake by L-GAB1 cells. Guvacine, 4-cis-hydroxynipecotic acid (4-cis-OHNA), 2,4-diaminobutyric acid (DABA) and (±)nipecotic acid (NA) have all been shown to be potent inhibitors of high-affinity GABA uptake in the CNS, with $IC_{50}$ values generally between 10–200 μM for both neuronal and glial uptake systems (Iversen & Kelly, 1975; Lester & Peck, 1979; Krogsgaard, 1980; Krogsgaard-Larsen et al., 1987). Each of these agents was used at several concentrations ranging from 1 to 100 μM in assays of [$^3$H] GABA uptake by L-GAB1 cells. (±)Nipecotic acid and DABA are the only inhibitors that exhibited some effect. Guvacine and 4-cis-OHNA were without measurable effect. The inhibitory effects of both NA and DABA seemed to saturate by 100 μM; inhibition in both cases was less than 20% of the total [$^3$H] GABA uptake by L-GAB1 cells. Other systems of high-affinity GABA uptake, on the contrary, have been reported to exhibit greater sensitivity to all four of these inhibitors. Thus, the pharmacological profile of the high-affinity GABA uptake system in L-GAB1 cells seems to be distinct from those characterized in the CNS to the following extent: (1) neither 4-cis-OHNA nor guvacine were able to mediate any inhibitory effect; (2) while NA and DABA both gave some inhibitory effects, the extent of each inhibition was small.

L-GAB1 cells were also analyzed in terms of their ligand-specificity in the high-affinity GABA uptake mechanism. The uptake system in L-GAB1 is fairly selective for GABA and not inhibited by the presence of any of the following neurotransmitters (each at 100-fold excess relative to the assay [$^3$H] GABA concentration): norepinephrine, epinephrine, glycine. This system is also not sensitive to the following amino acids: L-aspartate, lysine, proline, serine, tryptophan, phenylalanine and tyrosine. The system is somewhat sensitive to the following amino acids: L-arginine, D-glutamate, L-glutamate, D-aspartate, L-alanine. Of these, L-glutamate seemed to be the most potent inhibitor because it resulted in almost complete inhibition, whereas the other amino acid inhibitors only resulted in partial inhibition.

Transfection of total human DNA into mouse L-M fibroblasts thus generated L-GAB1, a clonal cell line which exhibits a high-affinity GABA uptake system (not present in L-M cells, and is an addition to the endogenous low-affinity GABA uptake system) which is both sodium- and chloride-dependent, pharmacologically distinct from the high-affinity GABA uptake systems previously characterized in the CNS, and possesses relative, but not absolute, ligand-specificity for GABA. This system is also sensitive to L-glutamate, the biosynthetic precursor of GABA.

EXAMPLE VII

Transgenic Cells Containing a High-Affinity D- And L-Aspartate (Asp) Transporter In our search for a transfectant, clonal cell line that manifests the sodium-dependent glutamate/aspartate co-transporter previously characterized in the CNS, we chose D-[$^3$H] aspartate (D-[$^3$H] Asp) as a suitable uptake ligand because it is resistant to intracellular enzyme activity which is responsible for degradation of intracellular L-glutamate and L-aspartate and therefore can be detected following uptake (Davies & Johnston, 1976; Cross et al., 1986).

Using the same approach as described above a clonal cell line, L-Asp1, was identified which possesses a higher degree of D-[$^3$H] Asp uptake than L-M cells (which exhibit very little D-[$^3$H] Asp uptake activity). Kinetic analyses of D-[$^3$H] Asp uptake for both L-M and L-Asp1 cells (double-reciprocal plot of the initial uptake velocities measured for each of several D-[H] Asp concentrations ranging from 0.1 to 10 $\mu$M) for L-M cells revealed a linear relationship with no positive y-intercept and no negative x-intercept, implying the absence of a definable uptake system within these concentrations of D-[$^3$H] Asp. In contrast, the double-reciprocal profile of L-Asp1 cells fit a linear relationship with a position y-intercept and a negative x-intercept. L-Asp1 cells thus possess a kinetically definable uptake mechanism for D-Asp that is absent in L-M cells. For L-Asp1 cells, transport $K_m = 10.3$ $\mu$M, transport $V_{max} = 35$ pmol/min/mg protein for D-[$^3$H] Asp uptake. This clearly indicates that the transport system in L-Asp1 cells is a high-affinity mechanism, and possesses an affinity for D-[H] Asp which is comparable to that of high-affinity glutamate/aspartate co-transporters previously identified in the CNS and in peripheral tissues (Davies & Johnston, 1976; Gazzola et al., 1981; Anand et al., 1986; Erecinska et al., 986; Wilson & Pastuszko, 1986; Cowburn et al., 1987; Debler & Lajtha, 987; Wingrove & Kimmich, 1987; Griffiths et al., 1989; Moe & Smith, 1989).

Ion-substitutions were done by replacing the NaCl content of the incubating Ringer's buffer with various chloride salts of monovalent cations and sodium salts of monovalent anions. Replacement of sodium by other monovalent cations resulted in decreased uptake activities. Similar substitutions of chloride, however, indicated no effect on uptake. Thus, the high-affinity uptake system in L-Asp1 cells is sodium-dependent and chloride-independent, which is consistent with findings for previously-characterized high-affinity uptake systems specific for aspartate/glutamate (Balcar & Johnston, 1972; Davies & Johnston, 1976; Gazzola et al., 1981; Erecinska et al., 1986; Cowburn et al., 1987; Wingrove & Kimmich, 1987; Moe & Smith, 1989).

The specificity of the high-affinity transport mechanism in L-Asp1 cells also was examined. All of the amino acids and amino acid-analogues tested, except L-aspartate, had no inhibitory effect on uptake of D-[$^3$H] Asp. Taurine, L-glutamine and L-cysteine seemed to each mediate some inhibition, but the extent of these inhibitions are slight and not statistically significant. This suggests that the high-affinity system in L-Asp1 cells is indeed specific for D-Asp relative to other amino acids. The inhibitory effect of L-Asp is consistent with the conclusion that the high-affinity system in L-Asp1 is indeed the aspartate/glutamate co-transport system. This is further verified when D-[$^3$H] Asp uptake by L-Asp1 cells is inhibited by unlabelled D-Asp, L-Asp and L-glutamate, but not D-glutamate, which are characteristics of the aspartate/glutamate co-transport system in the CNS (Cowburn et al., 1987).

The high-affinity transport system in L-Asp1 cells was also analyzed in terms of its relative sensitivity to compounds specific for various subtypes of excitatory amino acid (EAA) receptors. Ligands specific for the NMDA-subtype of EAA receptors (including NMDA and L-homocysteic acid (LHCA)) and quisqualate-subtype of EAA receptors (including quisqualate (QA) and glutamate diethylester (DEEG)) were all without effect. Both kainate and dihydroxykainate (ligands for the kainate-subtype of EAA receptors) mediated significant inhibition. This is consistent with previous findings on inhibitory effects of kainate analogues on high-affinity D-Asp uptake (Anand et al., (1986).

A series of known inhibitors of high-affinity D-Asp uptake systems (including L-cysteic acid (L-CA), L-cysteine sulfinic acid (L-CSA), aminophosphonopropionic acid (APPA) and D-threoaspartic acid (THAA)) were also tested for their effects on D-[$^3$H] Asp uptake by L-Asp1 cells. Of these compounds, L-CA, L-CSA and THAA exhibited potent inhibitory effects, while APPA was moderate in inhibitory potency. a-aminoadipic acid (AAA), an inhibitor of the cysteine glutamate exchange system, was virtually without inhibitory effect. These observations are all consistent with these compounds' reported effects on high-affinity aspartate/glutamate co-transport systems characterized in the CNS (Anand et al., 1986).

Thus, transfection of total human DNA into mouse L-M fibroblasts generated a clonal cell line, L-Asp1, which possesses a high-affinity D-[$^3$H] Asp uptake system with the following characteristics: (1) sodium dependent and chloride-independent; (2) specific for only D-Asp, L-Asp, L-Glu and none of the other amino acids or amino acid-analogues; (3) sensitive only to kainate and kainate-analogues, and not ligands specific for any other EAA receptor-subtype; (4) sensitive to various known inhibitors of high-affinity aspartate/glutamate co-transport system. These characteristics collectively indicate that the high-affinity system in L-Asp1 cells is, by every criterion examined, comparable to the high-affinity aspartate/glutamate co-transport system found in the CNS.

It is evident from the above results that novel methods and compositions are provided for genetic reconstitution of membrane transport systems. The availability of cell lines which express high-affinity neurotransmitter uptake in physiological, kinetic and pharmacological mimicry of known high-affinity uptake systems provide a number of unique advantage not offered by other preparations of neurotransmitter uptake. Such cell lines are monoclonal in origin and evidently devoid of most neurotransmitter receptor subtypes, therefore their membrane composition and uptake characteristics are relatively invariant over time. Thus, an important new tool is provided for dissecting the mechanism of neurotransmitter transport, while also allowing for rapid and reliable screening of a large number of compounds to identify novel candidates, due to their ability to bind to the high-affinity transporter (and either be transported intracellularly or compete with endogenous compounds bound by the transporter), and therefore potentially useful in the clinical treatment of certain diseases.

All publications and patent applications mentioned in this specification are indicative of the level of skill of those skilled in the art to which this invention pertains. All publication and patent applications are herein incorporated by reference to the same extent as if each individual publication or patent application was specifically and individually indicated to be incorporated by reference.

The invention now being fully described, it will be apparent to one of ordinary skill in the art that many changes and modification can be made thereto without departing from the spirit or scope of the appended claims.

What is claimed is:

1. An in vitro culture of mammalian cells consisting essentially of:
    cells transformed with a human DNA encoding a neurotransmitter transporter selected from the group consisting of a transporter for γ-aminobutyric acid, serotonin, and glycine, with the proviso that when said cells are human cells, said DNA is heterologous to said cells.

2. The mammalian cells according to claim 1, wherein said cells are cells of the genus rodentiae.

3. The mammalian cells according to claim 1, wherein said cells are other than cells associated with brain tissue.

4. A composition consisting essentially of:
    an in vitro culture of primate mammalian cells comprising human DNA encoding a neurotransmitter transporter selected from the group consisting of a transporter for γ-aminobutyric acid, serotonin and glycine, wherein uptake of a neurotransmitter into said cells via said transporter is characterized as sodium ion dependent, kinetically saturable and temperature sensitive, with the proviso that when said cells are human cells, said DNA is heterologous to said cells.

5. The composition according to claim 4, wherein said uptake is further characterized as being at least substantially inhibited by known agonists or antagonists of said neurotransmitter transporter.

6. The composition according to claim 4, wherein said uptake is further characterized as being of high-affinity.

7. The composition according to claim 1, wherein said cells are mouse fibroblast cells.

8. The composition according to claim 6, wherein said cells further comprise a gene providing for resistance to a cytotoxic agent resistance gene.

9. A culture of mouse cells in vitro and cells and cultures derived therefrom comprising:
    said cells having integrated into the genome a human DNA encoding a neurotransmitter transporter selected from the group consisting of a transporter for γ-aminobutyric acid, serotonin, and glycine, said cells produced by the method of transforming mouse cells with said DNA by calcium phosphate precipitation and selecting for transfectants by means of a selection marker on a co-transfected plasmid.

10. A method for determining whether a candidate compound has an effect on neurotransmitter uptake as an inhibitor or an enhancer of neurotransmitter uptake, said method consisting essentially of:
    contacting cells according to claims 1, 5, or 9
    a. said candidate compound and a neurotransmitter comprising a detectable label; or
    b. a neurotransmitter comprising a detectable label;
    normalizing to the same number of cells the amount of label detectable in transgenic cells contacted with (a) and (b); and
    comparing the amount of normalized label detectable in transgenic cells contacted with (a) with the amount of normalized label detectable in transgenic cells contacted with (b), wherein where said amount of normalized label detectable in cells contacted with (b) is greater than said amount of normalized label detectable in cells contacted with (a) is indicative that said candidate compound is an inhibitor of neurotransmitter uptake, or wherein where said amount of normalized label detectable in cells contacted with (a) is greater than said amount of normalized label detectable in cells contacted with (b) is indicative that said compound is an "enhancer" of neurotransmitter uptake.

11. The method according to claim 10 wherein said cells contacted with said (a) are contacted with said candidate compound prior to being contacted with said neurotransmitter.

12. A method for determining whether a candidate compound is an agonist or an antagonist of neurotransmitter uptake, said method consisting essentially of:
    contacting cells according to claims 1, 5 or 9
    a. said candidate compound and a neurotransmitter comprising a detectable first label; or
    b. a neurotransmitter comprising a first detectable label; or
    c. said candidate compound comprising a detectable second label and unlabelled neurotransmitter; or
    d. said candidate compound comprising a detectable second label;
    wherein said first label and said second label may be the same or different;
    normalizing to the same number of cells the amount of label detectable in transgenic cells contacted with (a), (b), (c), and (d); and comparing the amount of normalized label detectable in transgenic cells contacted with (a) with the amount of label detectable in transgenic cells contacted with (b); and the amount of label present in transgenic cells contacted with (c) with the amount of label detectable in transgenic cells contacted with (d), wherein where said amount of normalized label detectable in cells contacted with (a) is greater than said amount of normalized label detectable in cells contacted with (b) and where said amount of normalized label detectable in cells contacted with (d) is greater than said amount of normalized label detectable in cells contacted with (c) is indicative that said candidate compound is an agonist of neurotransmitter uptake, and where said amount of normalized label detectable in cells contacted with (b) is greater than said amount of normalized label detectable in cells contacted with (a) and where said amount of normalized label detectable in cells contacted with (c) is greater than said amount of normalized label detectable in cells contacted with (d) is indicative that said candidate compound is an antagonist or neurotransmitter uptake.

* * * * *